(12) United States Patent
Toujo et al.

(10) Patent No.: US 8,426,627 B2
(45) Date of Patent: *Apr. 23, 2013

(54) PHOSPHORYLCHOLINE GROUP-CONTAINING COMPOUND AND SURFACE MODIFYING AGENT COMPOSED OF SUCH COMPOUND

(75) Inventors: Yousuke Toujo, Yokohama (JP); Kazuyuki Miyazawa, Yokohama (JP); Taketoshi Kanda, Yokohama (JP); Hiroshi Kutsuna, Yokohama (JP); Kenichi Sakuma, Yokohama (JP); Masayoshi Wada, Yokohama (JP); Yukimitsu Suda, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 138 days.

This patent is subject to a terminal disclaimer.

(21) Appl. No.: 12/955,086

(22) Filed: Nov. 29, 2010

(65) Prior Publication Data
US 2011/0130583 A1 Jun. 2, 2011

Related U.S. Application Data

(62) Division of application No. 10/580,874, filed as application No. PCT/JP2004/017835 on Dec. 1, 2004, now Pat. No. 7,906,670.

(30) Foreign Application Priority Data

Dec. 2, 2003 (JP) .................................. 2003-402725
Nov. 30, 2004 (JP) .................................. 2004-345739

(51) Int. Cl.
*C07F 9/02* (2006.01)
(52) U.S. Cl.
USPC .......................................... 556/405; 556/413
(58) Field of Classification Search .................. 556/405, 556/413
See application file for complete search history.

(56) References Cited

U.S. PATENT DOCUMENTS 5,573,694 A * 11/1996 Danner ......................... 252/8.63
7,875,692 B2 * 1/2011 Miyazawa et al. .............. 528/28
7,906,670 B2 * 3/2011 Toujo et al. .................... 556/405

FOREIGN PATENT DOCUMENTS

WO   WO 2004/048492 A1 *  6/2004

OTHER PUBLICATIONS

Lu, J.R.; Murphy; E.F.; Su, T.J.; Lewis, A.L.; Stratford, P.W. Langmuir, 2001, 17, 3382-9.*

* cited by examiner

*Primary Examiner* — Porfirio Nazario Gonzalez

(57) ABSTRACT

A phosphorylcholine group-containing chemical compound represented by the following formula (1):

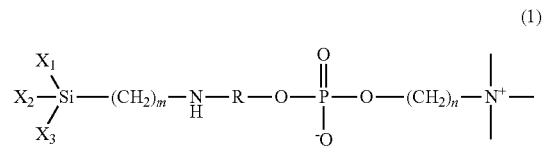

(1)

wherein, m denotes 2-6 and n denotes 1-4, $X_1$, $X_2$, and $X_3$, are independent of each other, and denote a methoxy group, ethoxy group, or halogen;

up to two of $X_1$, $X_2$, and $X_3$ can be any of the following groups: a methyl group, ethyl group, propyl group, isopropyl group, butyl group, or isobutyl group:

R is a structure represented by the following formula (2) (the chemical compound of formula (1) in the structure of formula (2) being expressed as A-R—B):

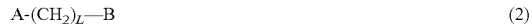

(2)

wherein, in formula formulas (2), L is 1-6.

4 Claims, 18 Drawing Sheets

PHOSPHORYLCHOLINE GROUP-CONTAINING COMPOUND AND SURFACE MODIFYING AGENT COMPOSED OF SUCH COMPOUND

CROSS REFERENCE TO A RELATED APPLICATIONS

This is a divisional patent application of co-pending application Ser. No. 10/580,874, filed Apr. 16, 2008, now allowed.

TECHNICAL FIELD

The present invention relates to a new chemical compound containing a phosphorylcholine group, a surface modifier consisting of said compound, modified powder modified by using said surface modifier, chromatography packing that uses said modified powder as a carrier, and glass experimental devices and filters modified by using said surface modifier.

The surface modifier consisting of the compound of the present invention gives biocompatibility, moisture retaining properties, and other various useful functions to objects.

BACKGROUND ART

Polymers having phosphorylcholine groups have been researched as biocompatible polymers, and biocompatible materials prepared by coating various base agents with such polymers have been developed.

For example, Patent Document 1 discloses a cosmetic in which powder coated with a homopolymer or copolymer of 2-methacryloyloxyethyl phosphorylcholine is used as cosmetic powder to improve moisture retention and adhesion to the skin.

Also, Patent Document 2 and Patent Document 3 disclose medical materials and a separation agent coated with polymers having phosphorylcholine groups.

The surface of the aforementioned materials are coated with a polymer obtained by polymerizing monomers having the phosphorylcholine structure prepared by reacting an acrylic-type monomer mainly having hydroxyl groups with 2-chloro-1,3,2-dioxaphosphorane-2-oxide and then using trimethylamine to turn the reaction product into a quaternary ammonium (refer to Patent Documents 4 and 5 for the preparation method).

Patent Document 4 describes the preparation of a copolymer of 2-methacroyloxyethylphosphorylcholine and methacrylate, and Patent Document 5 describes the preparation of a homopolymer of 2-methacryloyloxyethyl phosphorylcholine.

On the other hand, there are many commercially available packings for GFC, which separates biological samples such as proteins and polypeptides that have smaller molecular weights than proteins by means of size exclusion. For the packings for GFC, there are packings that use cross-linked hydrophilic polymers as the carrier and packings that use silica gel as the carrier.

A packing that uses a cross-linked hydrophilic polymer as the carrier has a wide pH range for the mobile phase and is highly versatile. However, compared with a packing that uses silica as the carrier, a packing that uses a polymer as the carrier is (1) harder to obtain a higher theoretical plate number due to the difficulty in controlling the fine pore size. Also, a packing that uses a polymer as the carrier is (2) often times incapable of obtaining chromatograms with good reproducibility due to an inferior strength against the high pressure applied when used for high-performance liquid chromatography (HPLC) and the swelling of the particles caused by the mobile phase solvent.

A packing that uses silica gel as the carrier has the problem of adsorption of proteins and/or polypeptides onto the surface of the silica gel carrier. To address this problem, there are packings commercially available that use silica gel whose surface is modified with non-dissociative hydrophilic groups for the purpose of suppressing the adsorption of proteins and/or polypeptides in the analysis sample onto the silica gel.

For example, Shodex PROTEIN KW-803 (product name) is commercially available from Showa Denko KK as a silica gel-type GFC column. This silica gel-type column is described in the catalogue as a silica gel-type GFC mode column suitable for analyzing proteins having a molecular weight of several thousands to a million.

Also, YMC-Pack Diol (product name) is commercially available from YMC Co. Ltd. This is also described as a silica gel-type GFC column prepared by chemically bonding functional groups having the diol structure to a silica gel carrier; it can be used to separate proteins having a molecular weight of ten thousand to several hundred thousand.

Non-Patent Document 1 reports a reduction in protein adsorption due to phosphorylcholine groups chemically grafted onto the carrier.

Patent Documents 6 and 7 disclose an organic silane type surface modifier (silane coupling agent) having the betaine structure, which is known to show excellent hydrophilicity. According to Patent Document 6, a silane coupling agent having sulfobetaine composed of the positive charge of the quaternary ammonium and the negative charge of sulfonic acid can be obtained by reacting dimethylaminoalkyl silane with 1,3-propanesulfone in an organic solvent. Patent Document 7 describes a method of manufacturing a silane coupling agent having carboxybetaine composed of quaternary ammonium and a carboxyl group. These silane coupling agents, when applied and dried on glass and such, can modify the surface of the object. However, although the betaine of such structures can give superior hydrophilicity to the object surface, electric neutrality is not achieved due to the uneven strength of the positive charge and the negative charge in betaine. For example, sulfobetaine is negatively charged due to the strong acidity of sulfonic acid and carboxybetaine shows a positive charge due to quaternary ammonium. The betaine structure of this kind has a very strong ion exchange interaction with protein, which leads to irreversible adsorption of the protein.

There is no example of these silane coupling agents used for chromatography packings and filters and experimental devices for the purpose of biocompatibility and/or protein adsorption suppression.

Patent Document 1: Japanese Patent Laid-Open H7-118123 bulletin
Patent Document 2: Japanese Patent Laid-Open 2000-279512 bulletin
Patent Document 3: Japanese Patent Laid-Open 2002-98676 bulletin
Patent Document 4: Japanese Patent Laid-Open H9-3132 bulletin
Patent Document 5: Japanese Patent Laid-Open H10-298240 bulletin
Patent Document 6: Japanese Patent Laid-Open H5-222064 bulletin
Patent Document 7: Japanese Patent Laid-Open S63-295593 bulletin
Non-Patent Document 1: Jian R. et al. Langmuir 2001, 17, 3382-3389

DISCLOSURE OF INVENTION

Problem that the Present Invention Aims to solve

However, it is difficult to effectively coat the entire surface by using a method that coats the object surface with a polymer having phosphorylcholine groups. Also, the polymer coating peels off the object's surface and may cause problems in terms of durability. Furthermore, since the object's surface is coated with the polymer, the effects may go beyond the purpose of giving biocompatibility by using phosphorylcholine groups and the basic characteristics required of the object itself, such as fine structures including pores, may be lost.

In the case of introducing a low molecular weight derivative of a phosphorylcholine group, if a functional group that can react with the derivative of the phosphorylcholine group is first introduced to the object and subsequently the phosphorylcholine group derivative is reacted, there will be unreacted functional groups left on the object's surface, which leads to a reduction in biocompatibility.

For example, if the amino group is first introduced onto the object's surface and subsequently an aldehyde derivative of phosphorylcholine is reacted with the amino group on the object's surface, then many unreacted amino groups will remain. These residual amino groups can be blocked to a certain extent by bonding another low molecular weight compound, but it is difficult to maintain hydrophilicity of the object's surface and also it is not possible to block all of them. When there are residual amino groups on the object's surface, since amino groups are strongly basic, acidic proteins have a strong ion-exchange type interaction with them, which mostly results in adsorption. When used for a chromatography packing, this worsens the recovery rate of the target protein and causes excessive tailing of the peaks. Furthermore, protein adsorption causes protein denaturation and, if used as a biocompatible material, causes irritation and such, which is not preferable.

The present invention is a result of the discovery that any desired amount of a phosphorylcholine group can be directly introduced onto the object's surface in an easy and highly versatile way by directly reacting a compound containing a phosphorylcholine group and a compound having a functional group that reacts with this compound and also a functional group that bonds with the object's surface.

And the inventors completed the present invention by discovering that a surface modifier consisting of said compound can be used to easily manufacture modified powder, chromatography packing that uses said modified powder as a carrier, and glass experimental devices and filters modified by using said surface modifier

Means to Solve the Problem

That is, the present invention provides a compound containing a phosphorylcholine group represented by the following general formula (1).

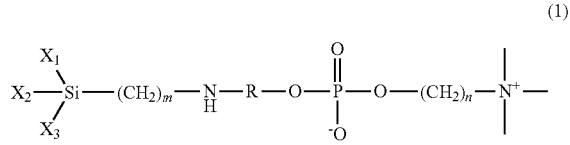

(1)

In this formula, m denotes 2-6 and n denotes 1-4.

$X_1$, $X_2$, and $X_3$, independent of each other, denote a methoxy group, ethoxy group, or halogen. Up to two of $X_1$, $X_2$, and $X_3$ can be any of the following groups: a methyl group, ethyl group, propyl group, isopropyl group, butyl group, or isobutyl group.

R is one of the structures in the following formulas (2)-(4) (the chemical compound of formula (1) in the structures of the following formulas (2)-(4) is expressed as A-R—B).

(2)

(3)

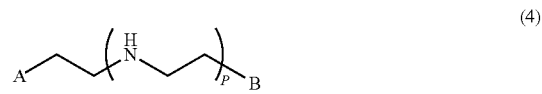

(4)

In formulas (2)-(4), L is 1-6, P is 1-3.

Also, the present invention provides a compound containing a phosphorylcholine group represented by the following general formulas (5) and (6).

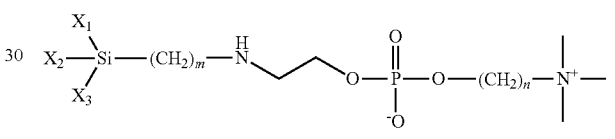

(5)

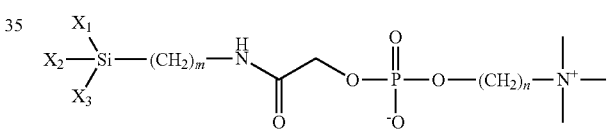

(6)

In this formula, m denotes 2-6 and n denotes 1-4. $X_1$, $X_2$, and $X_3$, independent of each other, denote a methoxy group, ethoxy group, or halogen. Up to two of $X_1$, $X_2$, and $X_3$ can be any of the following groups: a methyl group, ethyl group, propyl group, isopropyl group, butyl group, or isobutyl group.

Also, the present invention provides a surface modifier consisting of the aforementioned compound containing a phosphorylcholine group.

In addition, the present invention provides a method of manufacturing the compound represented by said formula (6) in which a compound having a phosphorylcholine group and a carboxyl group is synthesized by means of an oxidation reaction of glycerophosphorylcholine using sodium periodate and ruthenium trichloride and synthesis is carried out by using a condensation agent on an organic silane compound having an amino group and the compound having a phosphorylcholine group and a carboxyl group.

Also, the present invention provides modified powder treated with the aforementioned surface modifier.

Also, the present invention provides a chromatography packing consisting of a modified carrier treated with the aforementioned surface modifier.

Furthermore, the present invention provides a filter treated with the aforementioned surface modifier.

Finally, the present invention provides a glass experimental device whose surface is treated with the aforementioned surface modifier.

Effects of the Invention

By using the compound of the present invention and the surface modifier consisting of said compound, any desired amount of a phosphorylcholine group can be introduced onto the surface of various objects with a very simple one-step reaction. As a result, modified powder having desired functions given by the phosphorylcholine group, chromatography packing that uses said modified powder as a carrier, and glass experimental devices and filters modified by using said surface modifier can be manufactured easily.

More specifically, the present invention makes it possible to easily and quantitatively introduce the phosphorylcholine group, which causes very little adsorption of proteins and polypeptides, onto the object's surface. Also, since no unreacted functional groups other than the phosphorylcholine group are introduced, it is possible to provide highly biocompatible materials.

When used for a chromatography carrier such as silica gel, it is a very superior GFC packing. The characteristic of the chromatography packing synthesized by using the surface modifier of the present invention is its superior ability to separate samples in the GFC mode based not only on the differences in the molecular weight but also on the differences in the isoelectric point and hydrophobicity.

Furthermore, since the ion-exchange properties and hydrophobicity can be adjusted according to the salt concentration and pH of the mobile phase, unique separation for each protein can be carried out. In addition, since proteins are not irreversibly adsorbed onto the powder surface, separation, fractionation and analysis can be done without denaturation or deactivation of the proteins.

When filters and glass experimental devices are treated with the surface modifier of the present invention, filters and glass experimental devices with very little protein adsorption can be obtained.

BEST MODE FOR CARRYING OUT THE INVENTION

The chemical compound of the present invention is capable of surface modification and provides the protein adsorption suppression effect and such regardless of whether it is purified or not.

The phosphorylcholine group-containing chemical compound represented by the following formula (1), (5), or (6) is a new chemical compound.

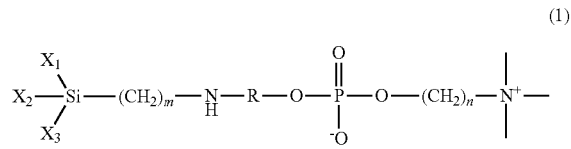

(1)

In this formula, m denotes 2-6 and n denotes 1-4.

$X_1$, $X_2$, and $X_3$, independent of each other, denote a methoxy group, ethoxy group, or halogen. Up to two of $X_1$, $X_2$, and $X_3$ can be any of the following groups: a methyl group, ethyl group, propyl group, isopropyl group, butyl group, or isobutyl group.

R is one of the structures in the following formulas (2)-(4) (the chemical compound of formula (1) in the structures of the following formulas (2)-(4) is expressed as A-R—B).

(2)

(3)

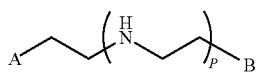

(4)

In formulas (2)-(4), L is 1-6, P is 1-3.

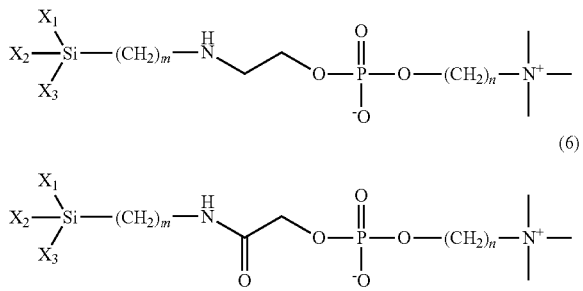

In this formula, m denotes 2-6 and n denotes 1-4. $X_1$, $X_2$, and $X_3$, independent of each other, denote a methoxy group, ethoxy group, or halogen. Up to two of $X_1$, $X_2$, and $X_3$ can be any of the following groups: a methyl group, ethyl group, propyl group, isopropyl group, butyl group, or isobutyl group.

"A Method of Preparing the Phosphorylcholine Group-Containing Chemical Compound of Formula (1), (5), or (6)"

The phosphorylcholine derivative shown in the following formula (7) is dissolved in distilled water. The phosphorylcholine derivative of the following formula (7) is a prior art chemical compound and commercially available.

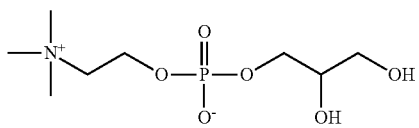

Figure 1:
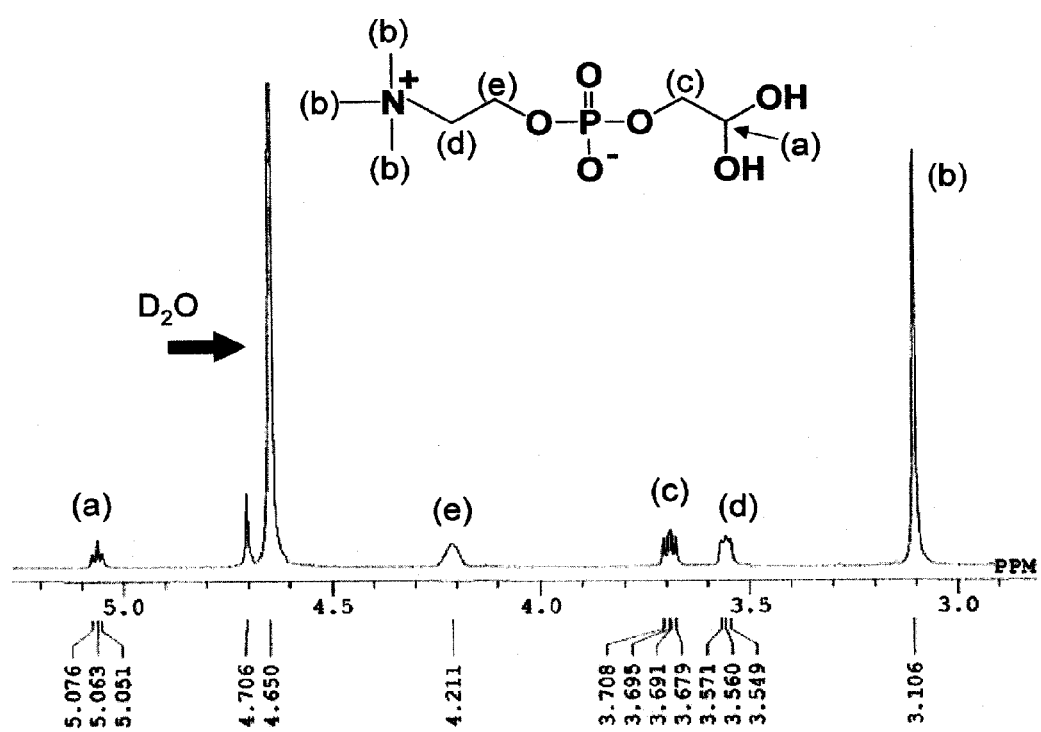
FIG. 1 is a 1H-NMR spectrum of the chemical compound prepared in Synthesis example 1.
Figure 18:
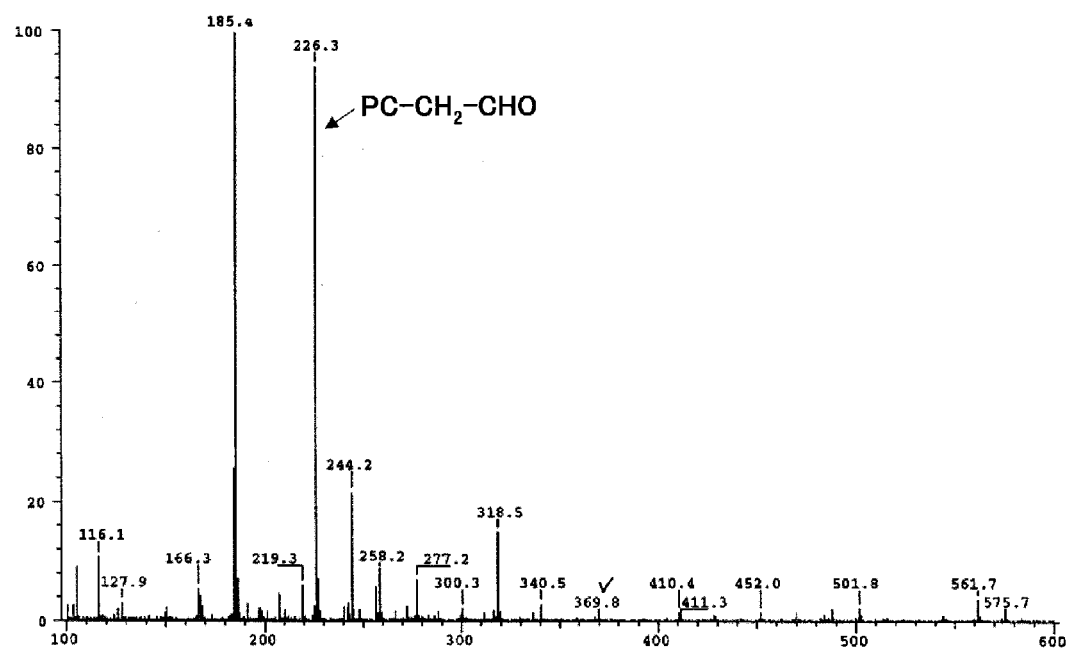
FIG. 18 is a mass spectrum of the chemical compound prepared in Synthesis example 1.

An aqueous solution of the chemical compound of formula (7) is cooled in an icy water bath; then sodium periodate is added, followed by five hours of stirring. The reaction fluid is concentrated under reduced pressure and dried under reduced pressure; methanol is used to extract a phosphorylcholine derivative having an aldehyde group shown in the following formula (8). The structural formula and the NMR spectrum are shown in FIG. 1 and the mass spectrum is shown in FIG. 18.

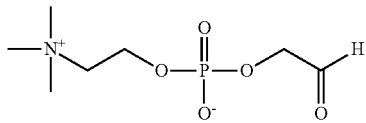

0.5 equivalents of 3-aminopropyltrimethoxysilane is added to a methanol solution of formula (8). This mixed solution is stirred for a prescribed amount of time at room temperature and cooled with ice; an appropriate amount of sodium cyanohydroborate is then added and the temperature is returned back to room temperature, followed by 16 hours of stirring. During this time dry nitrogen is continued to be fed through the reaction vessel. After filtering the precipitate, a methanol solution of formula (5) and/or (6) is obtained.

A purification method of the chemical compound of the present invention is described below. Purification methods of the chemical compound of the present invention are not limited to the following.

The obtained methanol solution is concentrated under reduced pressure and the residue is dissolved in distilled water. This aqueous solution is used as a sample. A high speed liquid chromatography column Capsule Pack SCX UG80 S-5 (size: 4.6 mm i.d.×250 mm) (from Shiseido), which is capable of the hydrophobic interaction and cation exchange, is connected to a HPLC apparatus and equilibrated with 0.2 mmol/L phosphate buffer (pH 3.5) at a flow rate of 1 mL/minute, followed by injection of 10 µL of the sample. A chromatogram can be obtained by using a differential refractometer as a detector, and the target chemical compound can be isolated.

However, the surface modifier consisting of the chemical compound of the present invention can be used as is at the methanol solution stage before purification.

The procedure described above can be carried out in the same way even when m and n in the chemical compounds represented by formula (5) or (6) change. The procedure shown here is for m=3 and n=2. Furthermore, a secondary amine can be inserted between the silane portion and the phosphorylcholine group by using 3-(2-aminoethylaminopropyl)trimethoxysilane and such for the silane compound having an amino group; this can be done with the same procedure as described above. The reaction solvent is not limited in particular; in addition to methanol, which was mentioned above, water, alcohols such as ethanol, propanol, and butanol, and aprotic solvents such as N,N-dimethylformamide and dimethylsulfoxide can be used. Note, however, that a dehydrated solvent is preferable to prevent polymerization of the organic silane compound during the reaction.

If a methoxy group ($OCH_3$) in formula (5) or (6) is replaced by an ethoxy group ($OC_2H_5$), then the reaction is carried out by using ethanol instead of methanol; if it is replaced by Cl, then dimethylformamide or dimethylsulfoxide is used instead.

Furthermore, even when one or two of the methoxy groups, ethoxy groups, or Cl's to be bonded to Si is replaced by a methyl group, ethyl group, propyl group, isopropyl group, or isobutyl group, the preparation can be carried out in the same manner as described above.

"Surface Modifier"

The chemical compounds of the aforementioned (5) and (6) are useful as a surface modifier for materials. That is, they modify the material surface by introducing a desired amount of the phosphorylcholine group. Specifically, for a material having hydroxyl groups on the surface, chemical bonds are formed by means of a dehydration reaction between the hydroxyl groups on the material surface and Si—$OCH_3$ of the compounds of formulas (5) and (6). This chemical reaction proceeds very easily and quantitatively in most organic solvents in the temperature range of 10-250° C. Chemically and physically very stable surface modification using phosphorylcholine groups can be carried out by means of this dehydration reaction.

When there is no hydroxyl group on the material surface, an effective method is to dissolve the compounds of formula (5) and (6) in a volatile solvent and apply the solution on the material surface, followed by drying of the solvent. In a specific example, the compounds of formulas (5) and (6) are dissolved in methanol and applied on the material surface. Next, methanol is evaporated in a temperature range of 10-250° C. An additional heating treatment is carried out as necessary. The Si—OCH$_3$'s of the compounds of formulas (5) and (6) can form Si—O—Si bonds through a dehydration reaction with each other and coat the material surface. The dehydration reaction through which Si—OCH$_3$'s form Si—O—Si bonds is a prior art. This membrane that forms when methanol evaporates makes bonds here and there with hydroxyl groups that exist in a minute amount on almost any material surface, which provides stable surface modification. This method is a very effective surface modification method not only for materials not having hydroxyl groups but also for materials having hydroxyl groups.

The material whose surface is modified with the surface modifier of the present invention becomes a material and molded piece having superior biocompatibility and hydrophilicity. This material can be used as a material having biocompatible phosphorylcholine groups directly on its surface in wide applications such as cosmetics, medical materials (artificial organs, surgical tools, etc.), chromatography packings, and paints.

Also, the surface modifier of the present invention is useful as a method to modify members that touch sample liquids, such as detector cells, sample vials, sampling needles, piping connectors, piping, etc. for separation or analytical apparatuses; materials for connecting piping of HPLC, MS, and NMR and capillary piping for electrophoresis apparatuses are particularly preferable for this modification method. Such materials include Teflon (registered trademark) tubes, Tefzel tubes, PEEK resin tubes, and fused silica tubes.

"A Method of Preparing the Compound Represented by Formula (6) Using a Phosphorylcholine Derivative Having a Carboxyl Group"

Phosphorylcholine derivatives have very high hydrophilicity and a very low solubility in organic solvents. Methods for synthesizing phosphorylcholine are largely divided into total synthesis methods whose starting material is dioxaphosphoranes and synthesis methods whose starting material is glycerophosphorylcholine obtained by the hydrolysis of phosphatidyl choline, which is a phospholipid contained in soy beans and such. Since only a limited selection of organic solvents can dissolve phosphorylcholine derivatives, the synthesis route becomes complex and the manufacturing cost is high, which is an obstacle for practical use. This problem of a complex synthesis process and the cost is prominent in total synthesis methods; however, the manufacturing method of the present invention can very easily prepare a phosphorylcholine derivative having a carboxyl group at a high yield in a good solvent for the phosphorylcholine derivative; in addition, glycerophosphorylcholine derived from phosphatidyl choline, which can be obtained inexpensively and in large quantities, can be used for manufacturing, which makes this method superior in terms of the cost, too. Finally, the compound represented by formula (6) can be obtained easily and at a high yield.

Figure 16:
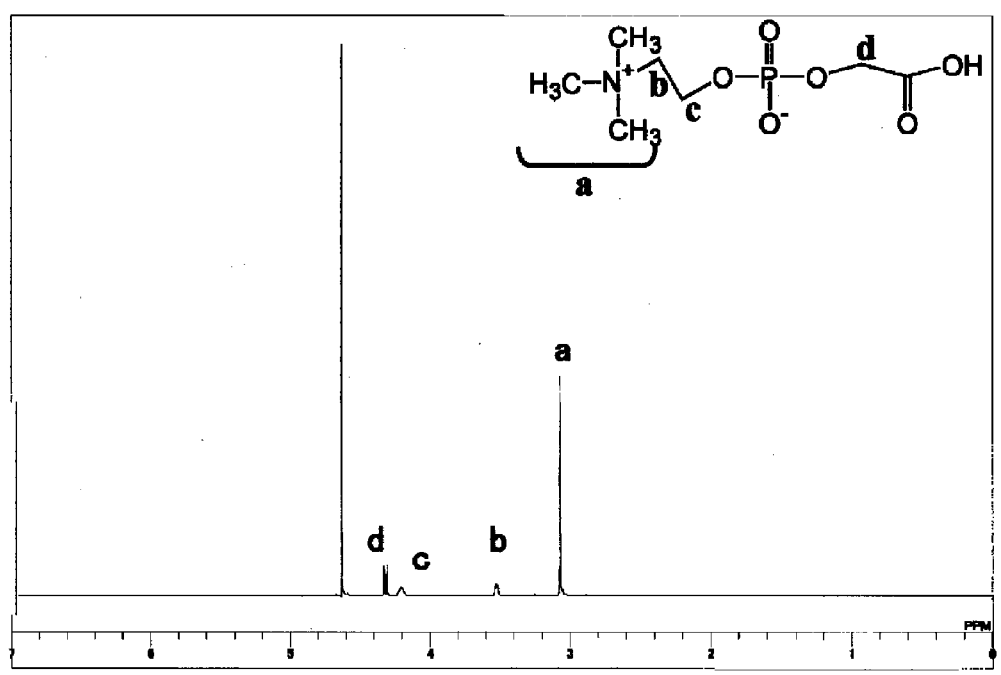
FIG. 16 is a 1H-NMR spectrum of the chemical compound prepared in Synthesis example 7.
Figure 17:
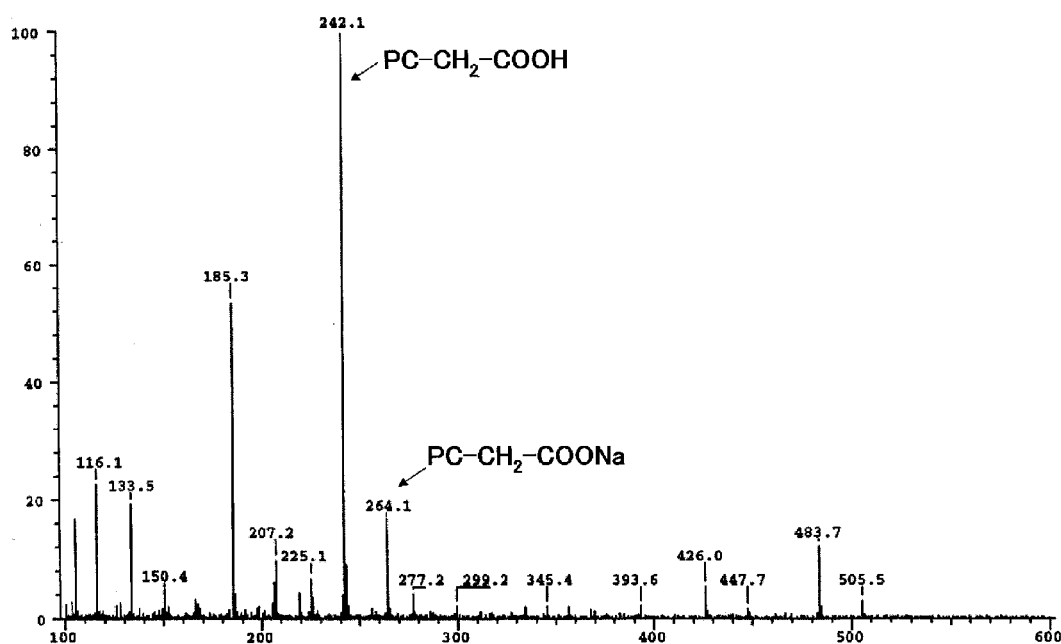
FIG. 17 is a mass spectrum of the chemical compound prepared in Example 7.

Glycerophosphorylcholine, sodium periodate, and ruthenium trichloride (hydrate) are added to an acetonitrile aqueous solution. After stirring at room temperature and filtration, the solvent is removed from the filtrate. The target substance is extracted from the obtained solid by using methanol and methanol is removed to obtain the phosphorylcholine derivative having a carboxyl group represented by the following formula (9). The structural formula and the NMR spectrum are shown in FIG. 16 and the mass spectrum is shown in FIG. 17.

Water can be used for the reaction solvent. In addition to sodium periodate, other periodates and periodic acid can be used. In addition to ruthenium trichloride, other divalent or trivalent ruthenium compounds and their hydrates can be used.

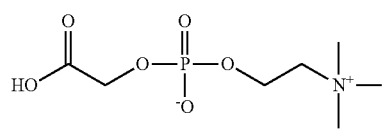

(9)

Next, 0.5 equivalents of 3-aminopropyltrimethoxysilane and one equivalent each of N-hydroxysuccine imide (NHS) and N-ethyl-N'-3-diaminopropylcarbodimide (EDC) are added to a methanol solution of the compound represented by formula (9). This mixed solution is stirred at room temperature for three hours to obtain the compound represented by formula (6).

For the reaction solvent, solvents other than methanol, such as N,N-dimethylformamide, dimethylsulfoxide, and chloroform, can be used. Not only NHS and EDC but also dicyclocarbodiimide (DCC) and carboxydiimidazole (CDI) can be used.

The procedure described above can be carried out in the same way even when m and n in the chemical compounds represented by formula (6) change. The procedure shown here is for m=3 and n=2. Note, however, that a dehydrated solvent is preferable to prevent polymerization of the organic silane compound during the reaction.

If a methoxy group (OCH$_3$) in formula (6) is replaced by an ethoxy group (OC$_2$H$_5$), then the reaction is carried out by using ethanol instead of methanol; if it is replaced by Cl, then dimethylformamide or dimethylsulfoxide is used instead.

Furthermore, even when one or two of the methoxy groups, ethoxy groups, or Cl's to be bonded to Si are replaced by a methyl group, ethyl group, propyl group, isopropyl group, or isobutyl group, the preparation can be carried out in exactly the same manner as described above.

"Modified Powder"

The surface modifier of the present invention can be used preferably to modify powder having hydroxyl groups.

The modified powder of the present invention is prepared by using the following method.

Modified powder directly having phosphorylcholine groups on the powder surface, i.e. modified powder onto whose surface phosphorylcholine groups are introduced by means of chemical bonds, can be easily prepared.

Compared with powder onto which phosphorylcholine groups are introduced by coating it with a polymer having phosphorylcholine groups, this modified powder has an advantage in that it does not lose the phosphorylcholine groups due to polymers peeling off. It also has an advantage in that the fine structure of the powder itself is not lost because there is no polymer coating. Specifically, the surface can be coated with phosphorylcholine groups without burying stereoscopic several nanometer-sized fine structures (such as micropores) by using the surface modifier of the present invention.

In the case of introducing a low molecular weight derivative of a phosphorylcholine group, if a functional group that can react with the derivative of the phosphorylcholine group is first introduced to the object and subsequently the phosphorylcholine group derivative is reacted, there will be unreacted functional groups left on the object's surface, which leads to a reduction in biocompatibility. For example, if an amino group is first introduced onto the object's surface and subsequently an aldehyde derivative of phosphorylcholine is reacted with the amino group on the object's surface, then many unreacted amino groups will remain. These residual amino groups can be blocked to a certain extent by bonding another low molecular weight compound, but it is difficult to maintain hydrophilicity of the object's surface and also it is not possible to block all of them. When there are many residual amino groups on the material's surface, since amino groups are strongly basic, acidic proteins have a strong electrical interaction with them, which mostly results in adsorption. When used for a chromatography packing, this worsens the recovery rate of the target protein and causes excessive tailing of the peaks. Furthermore, protein adsorption causes protein denaturation and, if used as a biocompatible material, causes irritation and such, which is not preferable.

When synthesizing the surface modifier of the present invention, an excessive amount of an aldehyde derivative of phosphorylcholine is added to an organic silane compound so that they react in the liquid phase. The reactivity between amino groups and aldehyde groups is very high and it is known that almost 100% of amino groups react with aldehyde when an excessive amount of aldehyde is added. Therefore, no unreacted amino groups are detected in the surface modifier of the present invention. Therefore, the surface modifier of the present invention is capable of introducing only phosphorylcholine groups onto the object surface without coexisting unreacted amino groups. Because of this, the biocompatibility is much superior than the methods involving a two-stage reaction in the solid phase, and powder with less protein adsorption can be obtained.

"A Method of Preparing Modified Powder"

20 mL of distilled water is added to 20 mL of a methanol solution of the compound of formula (5) or (6), concentration 0.3 mmol/mL, and powder whose surface is to be modified is added. The mass of the powder needs to be adjusted according to its specific surface area. For example, for powder having a specific surface area of 100 $m^2/g$, the amount to be added should be about 10 g. This powder dispersion liquid is refluxed in an oil bath at 80° C.; after five hours, the powder is filtered and rinsed with methanol, followed by drying under reduced pressure at 80° C. for three hours, to obtain the modified powder.

The selection of the powder to be used is not limited in particular. Depending on the application, this generally means any object having an average particle size of 0.01-10 micrometers or 0.01-1000 micrometers. Specific examples include inorganic powders (for example, talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, tungstic acid metal salt, magnesium, silica, zeolite, barium sulfate, firing calcium sulfate (calcined gypsum), calcium phosphate, fluorine-apatite, hydroxy apatite, ceramic powder, metallic soaps (for example, zinc myristate, calcium palmitate, and aluminum stearate), boron nitride, and cerium oxide); organic powders (for example, polyamide resin powder (nylon powder), polyethylene powder, polymethylmethacrylate powder, benzoguanamine resin powder, polytetrafluoroethylene powder, polymethylsilsesquioxane powder, silicone elastomer powder, and cellulose powder); inorganic white pigments (for example, titanium dioxide and zinc oxide); inorganic red pigments (for example, iron oxide (red iron oxide) and iron titanate); inorganic brown pigments (for example, γ-iron oxide); inorganic yellow pigments (for example, yellow iron oxide and loess); inorganic black pigments (for example, black iron oxide and low-order titanium oxide); inorganic purple pigments (for example, manganese violet, cobalt violet); inorganic green pigments (for example, chromium oxide, chromium hydroxide, and cobalt titanate); inorganic blue pigments (for example, ultramarine blue and Berlin blue); pearl pigment (for example, titania coated mica, titania coated bismuth oxychloride, titania coated talc, coloration titania coated mica, bismuth oxychloride, fish scale flakes); metal powder pigments (for example, aluminum powder, copper powder); organic pigments such as Zr, barium or aluminum rake (for example, organic pigments such as red 201, red 202, red 204, red 205, red 220, red 226, red 228, red 405, orange 203, orange 204, yellow 205, yellow 401 and blue 404, as well as red 3, red 104, red 106, red 227, red 230, red 401, red 505, orange 205, yellow 4, yellow 5, yellow 202, yellow 203, green 3 and blue 1; and natural colors (for example, chlorophyll and β-carotene).

Using the aforementioned preparation method, powder containing a desired amount of hydrophilic phosphorylcholine groups is easily obtained. When the powder is a synthetic polymer, its hydrophilic portion may include a carboxylate group, hydroxyl group, primary-tertiary amine group, sulfonate group, phosphate group, polyoxyethylene group, ammonium group, amide, carboxybetaine, and saccharide, and the type and content of these in the powder can be adjusted to design its functions. For the hydrophobic portion, depending on the application, straight chain or branched alkyls having 2-22 carbon atoms, cyclic alkyls such as cholesterol, alkyl groups containing unsaturated bonds such as oleyl, hydrocarbon type aromatics such as benzene rings, naphthalene rings, and pyrene, hetero type aromatics such as pyridine rings, imidazole, thiazole, and indole, and hydrophobic groups such as perfluoroalkyl and polyalkylsiloxane can be contained; the selection can be made based on the application of the powder. The hydrophobic group of the synthetic polymer powder can bond directly to the polymer main chain with the ester, ether, amide, urethane, or urea bond, or indirectly via a spacer. Examples of the spacer include hydrophilic polyethyleneoxide, hydrophobic polypropyleneoxide, and straight chain alkyls having 2-22 carbon atoms.

The modified powder of the present invention is a powder having superior hydrophilicity and moisture retention. This can be used as biocompatible powder in a wide range of applications such as cosmetics, medical materials, chromatography packings, and paints.

"Chromatography Packing Consisting of a Modified Carrier Treated with a Surface Modifier"

By using the surface modifier of the present invention, chromatography packing having a desired amount of phosphorylcholine groups can be easily prepared by modifying the carrier surface.

Specifically, phosphorylcholine groups are introduced onto the carrier surface by means of a dehydration reaction between hydroxyl groups present on the carrier surface and Si—$OCH_3$ of the compounds of formulas (5) and (6).

20 mL of distilled water is added to 20 mL of a methanol solution of the compounds of formulas (5) and (6) (0.3 mmol/mL), and 4 g of spherical highly pure silica gel having an average particle size of 5 micrometers, average pore size of 300 angstroms, and specific surface area of 100 $m^2/g$ is added. This powder dispersion liquid is refluxed in an oil bath at 80° C.; after five hours, the powder is filtered and rinsed with methanol, followed by drying under reduced pressure at 80° C. for three hours, to obtain powder having phosphorylcholine groups directly on the surface.

For the reaction solvent, in addition to the water/methanol mixed solvent, protic solvents such as water, ethanol, and 2-propanol, and aprotic solvents such as dimethylsulfoxide, dimethylformamide, toluene, and diethyl ether can be used individually or in combinations.

When there is no hydroxyl group on the carrier surface, an effective method is to dissolve the compounds of formula (5) and (6) in a volatile solvent and apply the solution on the material surface, followed by drying of the solvent. Specifically, an appropriate amount, according to the specific surface area of the material, of a methanol solution of the compounds of formulas (5) and (6) (0.3 mmol/mL) is directly applied on the material. Next, methanol is evaporated in a temperature range of 10-250° C. The Si—$OCH_3$'s of the compounds of formulas (5) and (6) can form Si—O—Si bonds through a dehydration reaction with each other and coat the material surface. This dehydration reaction is a prior art. This membrane that forms when methanol evaporates makes bonds here and there with hydroxyl groups that exist in a minute amount on almost any material surface, which provides stable surface modification. This method is a very effective surface modification method not only for materials not having hydroxyl groups but also for materials having hydroxyl groups.

The largest difference between a method in which amino groups are introduced onto the carrier surface first and the compound containing the aldehyde derivative obtained by the oxidative ring-opening reaction of glycerophosphorylcholine is introduced and a method in which the surface modifier of the present invention is used is the presence/absence of unreacted amino groups on the material surface.

That is, when the surface modifier of the present invention is used, only phosphorylcholine groups can be introduced onto the material surface on the material surface without coexisting unreacted amino groups. In the case of introducing amino groups onto the powder surface in advance, the aldehyde derivative of glycerophosphorylcholine in the liquid phase has to react with amino groups on the solid surface and therefore the reaction rate is low because of diffusion control, steric hindrance due to the stereoscopic structures on the solid surface, stereoscopic properties of the phosphorylcholine group itself, etc. Phosphorylcholine groups can be introduced only to approximately 30% of the amino groups. The residual amino groups can be blocked to a certain extent by bonding another low molecular weight compound, but it is difficult to maintain hydrophilicity of the object's surface and also it is not possible to block all of them.

Also, when there are many residual amino groups on the material's surface, since amino groups are strongly basic, acidic proteins have a very strong electrical interaction with them, which mostly results in adsorption. When used for a chromatography packing, this worsens the recovery rate of the target protein and causes excessive tailing of the peaks. Furthermore, protein adsorption causes protein denaturation and, if used as a biocompatible material, causes irritation and such, which is not preferable.

In contrast, when synthesizing the surface modifier of the present invention, an excessive amount of an aldehyde derivative of phosphorylcholine is added to an organic silane compound and these two react in the liquid phase. The reactivity between the amino group and the aldehyde group is very high, and it is generally known that almost 100% of amino groups react with aldehyde if aldehyde is added in excess.

Therefore, no amino groups are detected in the surface modifier of the present invention. As a result, only phosphorylcholine groups can be introduced onto the object's surface without coexisting unreacted amino groups by using the surface modifier of the present invention. Because of this, powder with much superior biocompatibility and less protein adsorption, compared with the method in which a two-step reaction is carried out on the solid phase, can be obtained.

Also, there is a known phenomenon in which, when surface modification is carried out by dispersing spherical powder in the liquid phase, structurally weak powder disintegrates during stirring. In this method, phosphorylcholine groups can be introduced directly onto the powder in a short time and in one step, therefore the power stirring time required is reduced to one forth or less compared with a method in which a two-step reaction is carried out on the solid phase, which makes it applicable to a wider range of powders in terms of the structure and material. Specifically, surface modification can be done on mechanically weak powder that has a fine pore size larger than 1,000 angstroms without damaging the powder configuration.

Examples of the carrier used in the present invention include inorganic porous substances such as silica, silica gel, activated carbon, zeolite, alumina, and clay minerals, and porous organic polymer resins. The carrier is preferably in a powder form. Preferable is spherical or crushed porous silica gel. The average particle size of the spherical porous silica gel is 1-200 micrometers, preferably 1-10 micrometers, and the average size of the fine pores on the spherical porous silica gel is 10-2000 angstroms, preferably 80-1000 angstroms; the specific surface area is 0.01-800 $m^2/g$, preferably 80-600 $m^2/g$.

When the packing for chromatography of the present invention is used for a GFC column, the adsorption of proteins and/or polypeptides is very small and a higher separation ability is demonstrated.

That is, the chromatography packing of the present invention is a column packing superior in terms of suppressing adsorption of proteins and polypeptides. Therefore, it can be applied to a mode in which proteins and polypeptides are separated by their difference in molecular weight (GFC mode).

Furthermore, the chromatography packing of the present invention is a column packing having a higher separation ability based not only on differences in the molecular weight of the samples but also on subtle differences in the electrical charge of the samples because of the dual electrical charge of the phosphorylcholine group. There hasn't been a case of introducing a functional group having a dual electrical charge for the purpose of suppressing adsorption of proteins and therefore the chromatography packing prepared by using the surface modifier of the present invention is a new type of column packing for GFC which did not exist before. This characteristic of having electrical charges not only allows a superior separation ability for proteins and polypeptides compared with separation based only on the difference in the molecular weight, but also allows an ability to control the interaction between the packing surface and proteins and/or polypeptides by changing the pH and/or the salt concentration of the mobile phase. Therefore, it is possible to retain proteins and/or polypeptides at will by optimizing the pH and/or the salt concentration of the mobile phase.

Since the GFC mode can separate and purify proteins and enzymes without deactivating them, a higher separation ability of the column packing of the present invention is expected to be useful in isolation of unknown biological samples and medical applications.

Specifically, the chromatography packing of the present invention is superior, for example, in the separation of proteins in human serum, the separation of polypeptides contained in samples obtained by means of tryptic digestion of proteins, and the separation/fractionation of unknown proteins contained in a living organism based on activity evaluation, when used as a column packing with a high separation ability and very little protein and polypeptide adsorption.

"A Filter Treated with the Surface Modifier"

When analyzing proteins contained in a biological sample, a pre-treatment is necessary to remove impurities originating from the living organism. Specifically, when the protein concentration in blood is to be measured, blood cells, platelets and such need to be removed beforehand by means of filtering, centrifugation and such. When filtering blood and such, there is a problem in that the quantitative accuracy of protein measurement is reduced due to the adsorption of proteins on the filter used. In addition, a container having a double layer structure that passes the sample through a membrane having fine pores using centrifugal force is also used commonly for concentration, desalting, solvent substitution, etc. of protein samples. Examples include Ultrafree-MC centrifugal filter unit (product name) (from Nihon Millipore). This filter unit is set up in such a way that the pre-concentration sample is put in the upper part and the lower part is facing toward the outside of the centrifuge; centrifugal force of 5,000 G is applied to achieve the filtration. Filtering membranes of such devices also have a problem in that the protein recovery rate sometimes drops almost down to 50%.

By modifying the filter surface with the compounds of formulas (5) and (6), a filter having very little protein adsorption can be obtained. Phosphorylcholine groups having a superior protein adsorption suppression ability can be easily introduced because the Si—OCH, in formulas (5) and (6) and the hydroxyl groups on the filter surface are bonded to each other through a dehydration reaction. This method is effective for a wide variety of materials since most filters used, made of metal, fiberglass, etc., have hydroxyl groups originating from oxides.

When there is no hydroxyl group on the material surface, an effective method is to dissolve the compounds of formula (5) and (6) in a volatile solvent and apply the solution on the material surface, followed by drying of the solvent. Specifically, the material is directly soaked in an appropriate amount, according to the specific surface area of the material, of a methanol solution of the compounds of formulas (5) and (6) (0.3 mmol/mL). Next, methanol is evaporated in a temperature range of 10-250° C. The Si—OCH$_3$'s of the compounds of formulas (5) and (6) can form Si—O—Si bonds through a dehydration reaction with each other and coat the material surface. This dehydration reaction is a prior art. This membrane that forms when methanol evaporates makes bonds here and there with hydroxyl groups that exist in a minute amount on almost any material surface, which provides a relatively tough surface modification. This method is a very effective surface modification method not only for materials not having hydroxyl groups but also for materials having hydroxyl groups.

When treating the surface of an object having fine pores, such as a filter, it is difficult to coat it with a prior art polymer having phosphorylcholine groups. This is mainly because the polymer clogs the fine pores and thereby reduces the ability of the filter. The use of a low molecular weight compound such as those represented by formulas (5) and (6) has made it possible to modify the carrier surface without damaging the structural characteristics, such as fine pores, of the carrier. Furthermore, durability is excellent because chemical bonding, rather than physical adsorption, occurs on the carrier surface.

"A Glass Experimental Device Treated with the Surface Modifier"

A glass experimental device means an experimental device such as a storage container, measuring device, a cell, a fractionation tip, or a syringe for sample fractionation. A treatment using the surface modifier of the present invention can provide an experimental device having very little protein adsorption.

EXAMPLES

Next, the present invention is described in detail by referring to Examples. The present invention is not limited to these Examples.

Synthesis Example 1

An Aldehyde Chemical Compound Containing a Phosphorylcholine Group

L-α-glycerophosphorylcholine (450 mg) is dissolved in 15 ml of distilled water and cooled in an ice water bath. Sodium periodate (750 mg) (from Wako Pure Chemical Industries, Ltd) was added, followed by five hours of stirring. The reaction fluid was concentrated under reduced pressure and dried under reduced pressure; methanol was then used to extract the target substance. The structure is shown in the following chemical formula (8). A 1H NMR spectrum of the compound of formula (8) is shown in FIG. 1 and its mass spectrum is shown in FIG. 18.

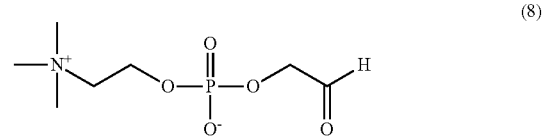

(8)

Example 1

Preparation of the Compounds of Formulas (5) and (6)

7.5 g of the compound of Synthesis example 1 was dissolved in 30 mL of dehydrated methanol, and the air inside the vessel was replaced by dry nitrogen. Next, 3.6 g of 3-aminopropyltrimethoxysilane (Shin-Etsu Chemical Co., Ltd.) was added to the methanol solution of chemical compound 1. This mixed solution was stirred for five hours at room temperature and cooled with ice; 2.5 g of sodium cyanohydroborate (from Wako Pure Chemical Industries, Ltd) was then added and the temperature was returned back to room temperature, followed by 16 hours of stirring. During this time dry nitrogen continued to be fed through the reaction vessel. After filtering the precipitation, a methanol solution of the target materials, i.e. the compound of the following formulas (10) and (11), was obtained.

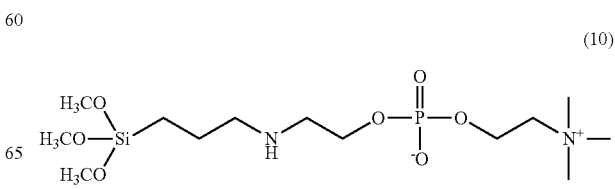

(10)

-continued

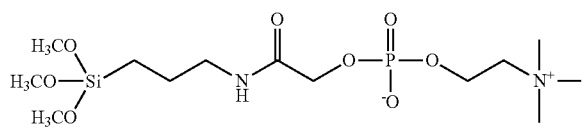

(11)

Example 2

Preparation of Modified Powder 35 mL of distilled water was added to a methanol solution containing the compound of formulas (10) and (11) prepared in Example 1, to which 14 g of silica gel having an average particle size of 5 micrometers, average fine pore size of 30 nm, and specific surface area of 140 m$^2$/g was added. This powder dispersion solution was refluxed for five hours at 80° C. After the refluxing, filtering and rinsing were carried out using 100 mL of methanol to obtain the target material.

Elemental analysis values of the modified powder treated in the procedure described above using the surface modifier of Example 1 are shown in Table 1. C % and N % in the table denote the mass % values of carbon and nitrogen contained in the powder. From these values, the atomicity ratio (C/N) of carbon and nitrogen in the powder treated with the surface modifier of Example 1 is calculated as 5.08. The C/N after all the methoxy group sites of the surface modifier of formulas (10) and (11) are bonded is five; this means the surface modifier is introduced onto the powder without being destroyed.

TABLE 1

| | Elemental analysis value | |
|---|---|---|
| | C % | N % |
| Powder before the surface modifier treatment | 0.06 | 0.03 |
| Powder after the surface modifier treatment | 3.95 | 0.91 |

Figure 2:
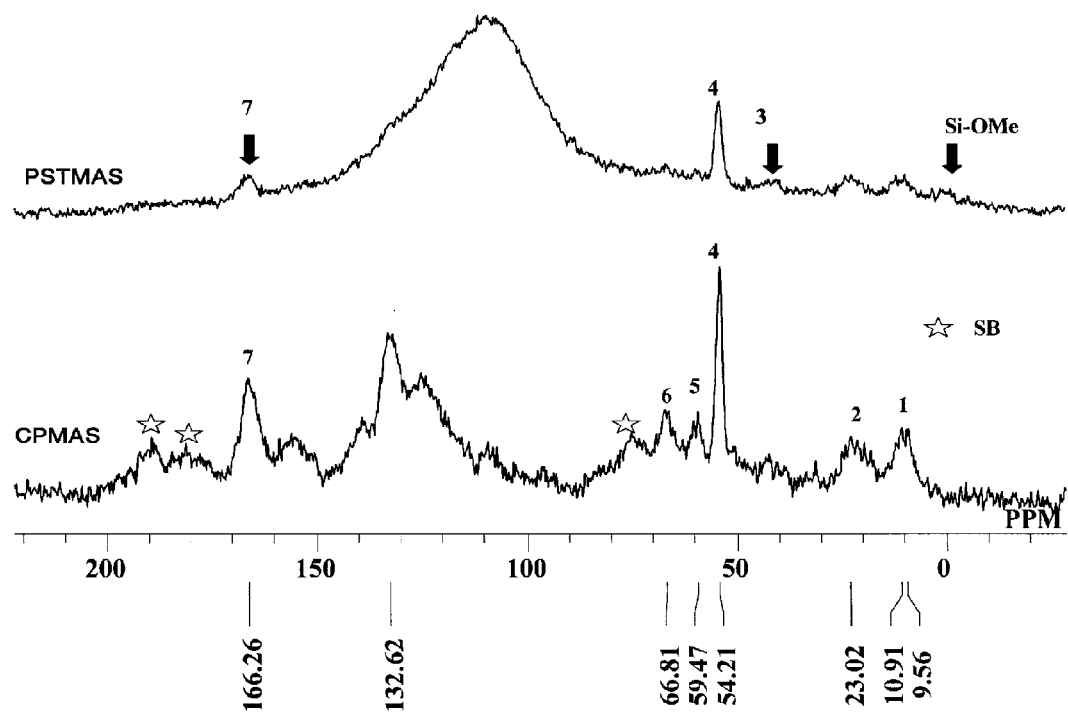
FIG. 2 is a 13C-CPMAS spectrum of the modified powder prepared in Example 2.

A 13C-CPMAS spectrum and a 13C-PSTMAS spectrum of this silica gel are shown in FIG. 2. The PSTMAS spectrum selectively captures a spectrum of free moving molecular chains; this method is widely used for analysis of modifying chains on the powder surface. In FIG. 2, a spectrum due to carbons in the choline group is observed at 54.2 ppm.

Figure 3:
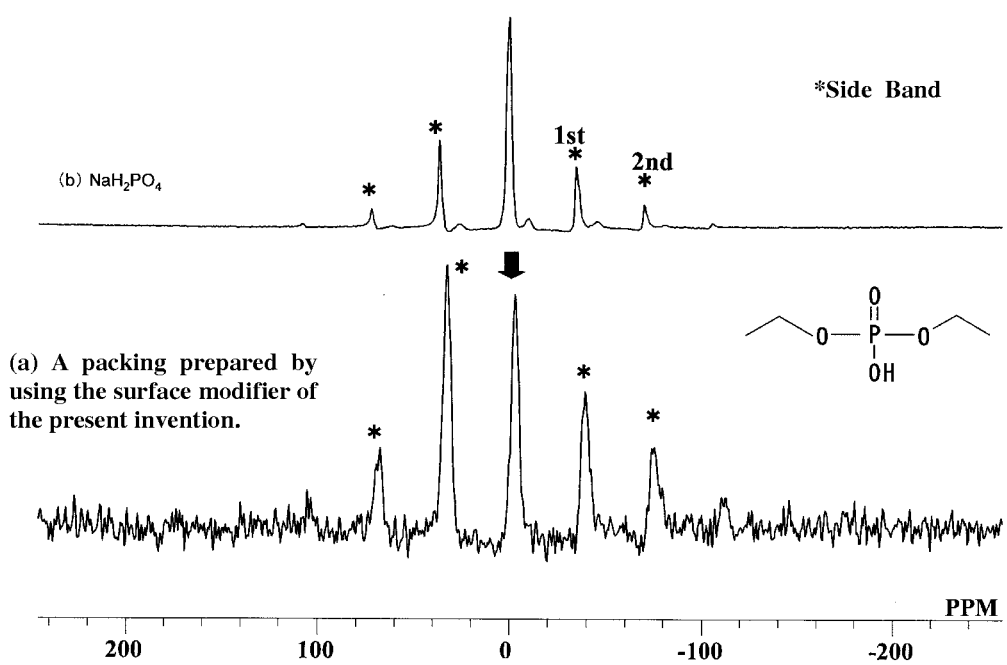
FIG. 3 is a 31P-CPMAS spectrum of the modified powder prepared in Example 2.

On the other hand, in the 31P-CPMAS spectrum of this silica gel shown in FIG. 3, peaks are detected at almost the same chemical shifts as NaH$_2$PO$_4$, which is measured as a control; this verifies the presence of phosphate groups. Since the presence of the choline group is verified by FIG. 2 and the presence of the phosphate group is verified by FIG. 3, it is believed that the phosphorylcholine group is introduced onto the carrier silica gel surface.

Furthermore, in FIG. 2, a spectrum due to propyls present between the silicon atom and the phosphorylcholine group are observed near 9 ppm and 23 ppm, and a spectrum due to ethyls in phosphorylcholine are observed near 60 ppm and 69 ppm. What is described above indicates that the structures of formulas (5) and (6) are introduced onto the silica gel without being destroyed. The bond between the phosphorylcholine group and propyltrimethoxysilane is a mixture of the secondary amine shown in formula (5) and the amide bond shown in formula (6).

Figure 4:
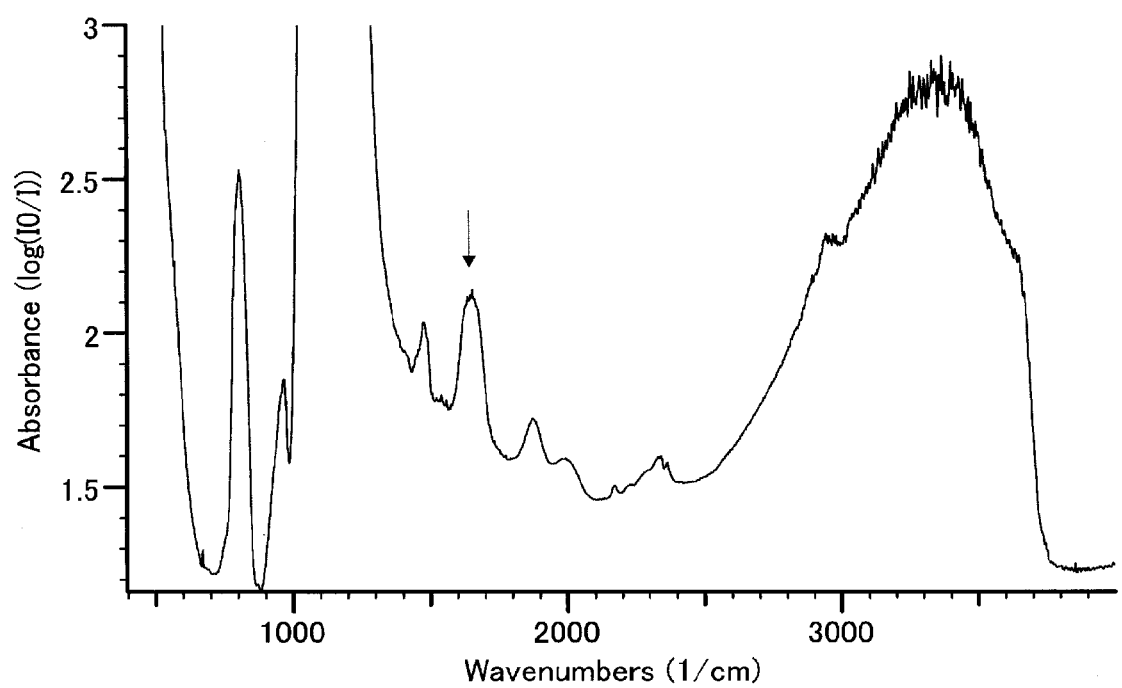
FIG. 4 is a FT-IR spectrum of the modified powder prepared in Example 2.

FIG. 4 shows a FT-IR spectrum of the modified powder synthesized in this Example. Absorption specific to amide bonding is observed near 1650 cm$^{-1}$.

Example 3

Chromatography Packing

Figure 5:
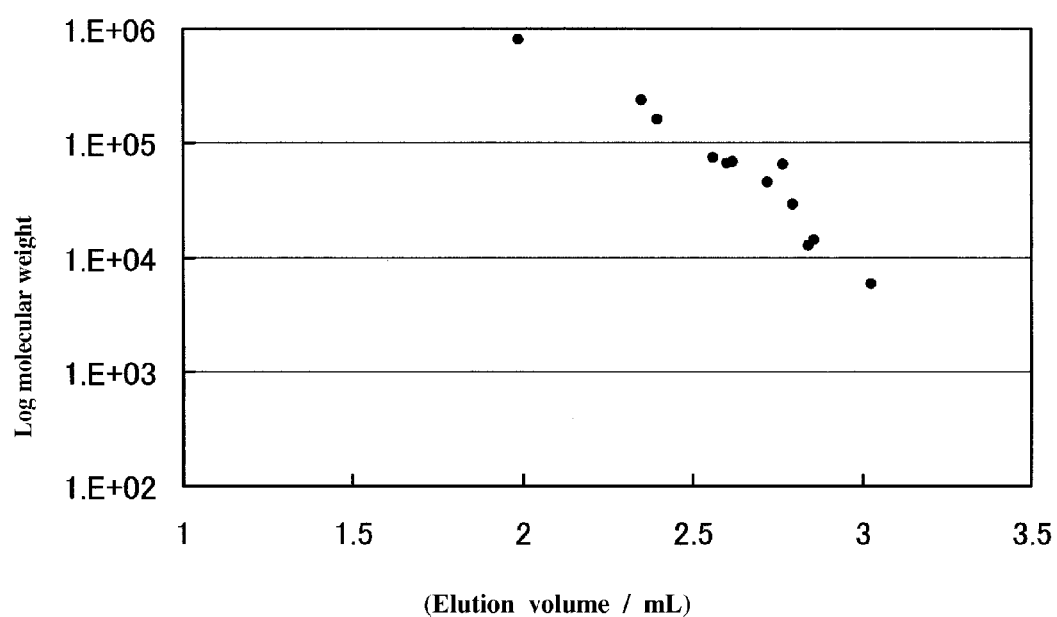
FIG. 5 is a calibration curve for the liquid chromatography packing prepared in Example 3 used in the GFC mode.
Figure 6:
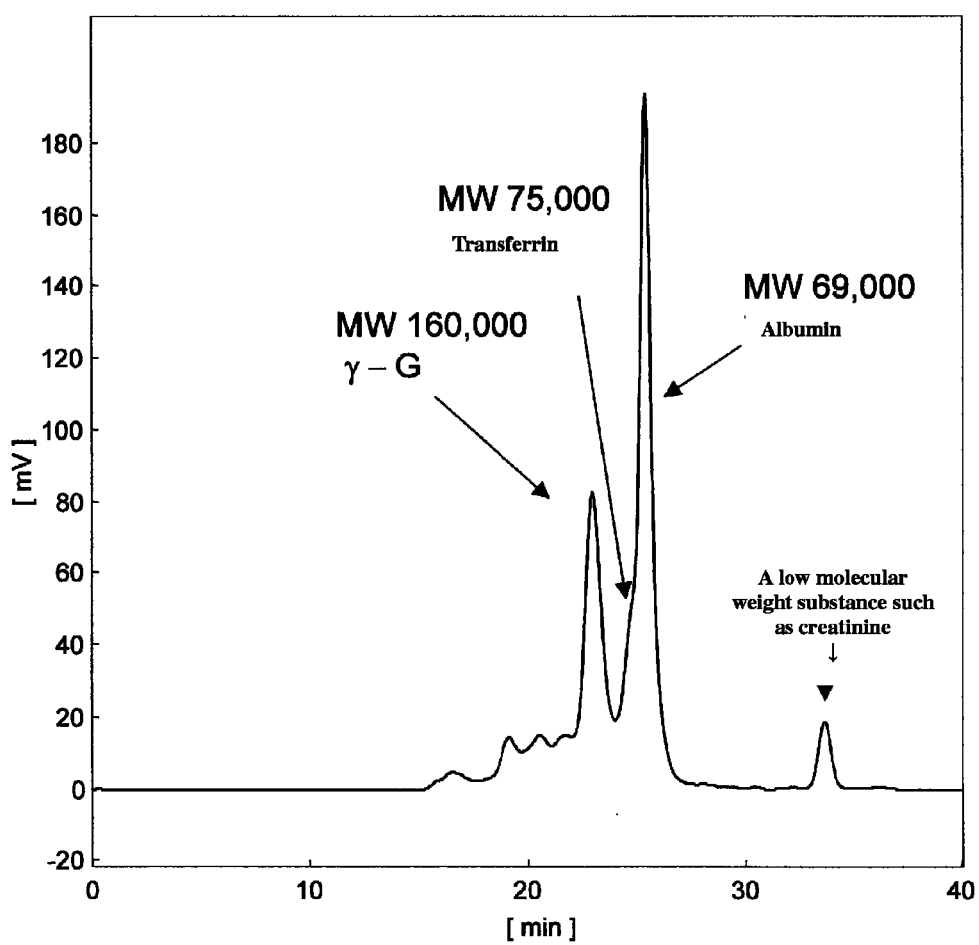
FIG. 6 is a chromatogram showing separation of human serum proteins by using the chromatography packing prepared in Example 3.

The modified powder prepared in Example 2, as a carrier, was put into an empty column having an inner diameter of 4.6 mm and a length of 250 mm by means of a common slurry method. Acquisition conditions of the chromatogram are as follows:

Mobile phase: 50 mmol/L phosphate buffer+500 mmol/L NaCl pH 6.8
Flow rate: 100 μL/min
Temperature: 25° C.
Detection: UV 280 nm A calibration curve for the column of Example 3 used under these conditions is shown in FIG. 5. The calibration curve shown in FIG. 5 has very good linearity within the measured range. Due to reduced adsorption of proteins, the interaction between the packing surface and proteins is very little, and as a result separation in the GFC mode, in which molecules having larger molecular weights elute faster, is observed. Next, the results from separating human serum proteins under the aforementioned conditions are shown in FIG. 6.

The sample used was Consera N (product name) diluted twice with distilled water; 2 μL of the sample was injected. GFC-mode separation in order of molecular weight occurs with an actual sample such as human serum as well, indicating a very high practical usefulness.

Comparative Example 1

Separation of proteins in a human serum sample (Consera N, product name, diluted two times with distilled water) was attempted by using a commercial chromatography column (Shodex PROTEIN KW803 from Showa Denko KK) off the shelf. The column in this Comparative example has the same inner diameter and length as the column mentioned in Example 3.

This packing is described as a packing for the size exclusion mode that has chemically bonded hydrophilic groups on the surface of porous silica gel. Its average pore size is 300 angstroms and the average particle size is 5 micrometers, which makes it preferable for comparison with the packing described in Example 1. It is described as suitable for separation of proteins having a molecular weight of 10,000 to several hundred thousand.

Shodex PROTEIN KW803 uses non-dissociative hydrophilic groups and therefore it does not have charged functional groups, unlike a packing prepared by using the surface modifier of the present invention. Therefore, very little ionic interaction with proteins are expected.

In the same manner as in Example 3, the separation of proteins in a human serum sample (Consera N, product name, diluted two times with distilled water) was attempted with the following setup: a 50 mmol/l phosphate buffer (prepared from Na$_2$HPO$_4$ and KH$_2$PO$_4$) having 500 mmol/l sodium chloride was used for the mobile phase and the flow rate is set at 0.1 ml/min and the column oven temperature at 25° C. The detection was done with the UV at 280 nm. The result is shown in FIG. 7(b).

For comparison, FIG. 7(a) shows a chromatogram for the same sample under the same conditions using a packing prepared by the surface modifier of the present invention obtained in Example 3.

Figure 7:
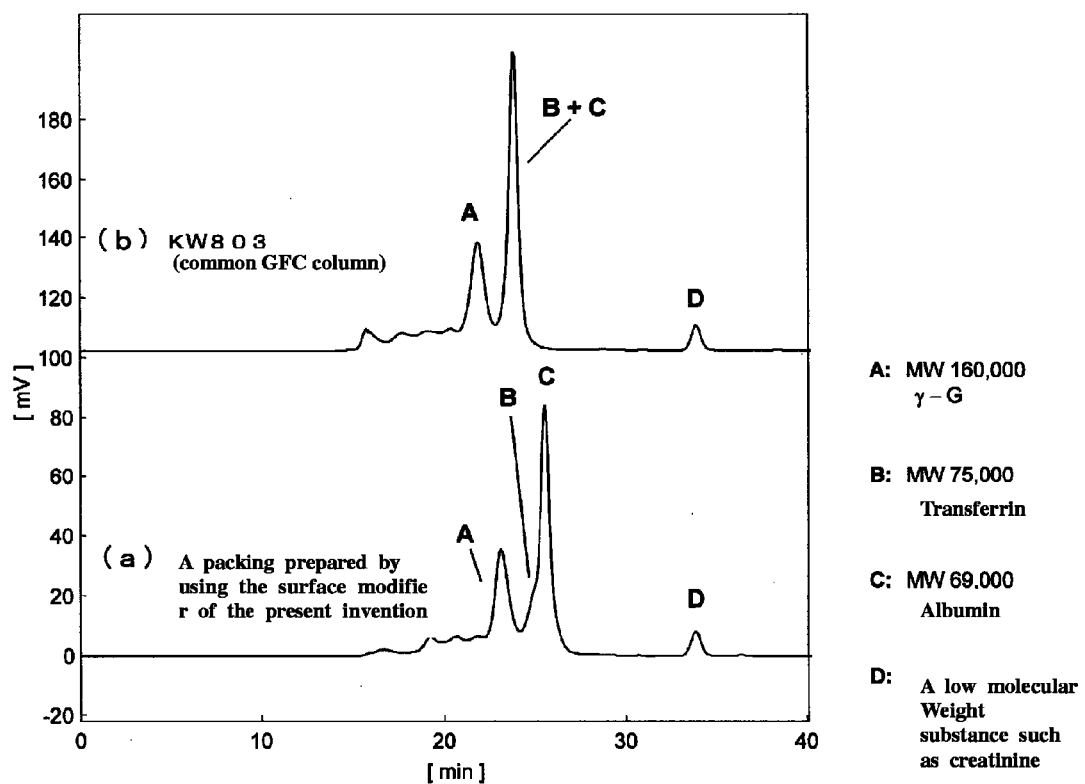
FIG. 7 is a chromatogram showing separation of human serum proteins wherein the mobile phase salt concentration is 500 mM. (a) A packing synthesized by using the surface modifier of the present invention. (b) Shodex PROTEIN KW803.
Figure 8:
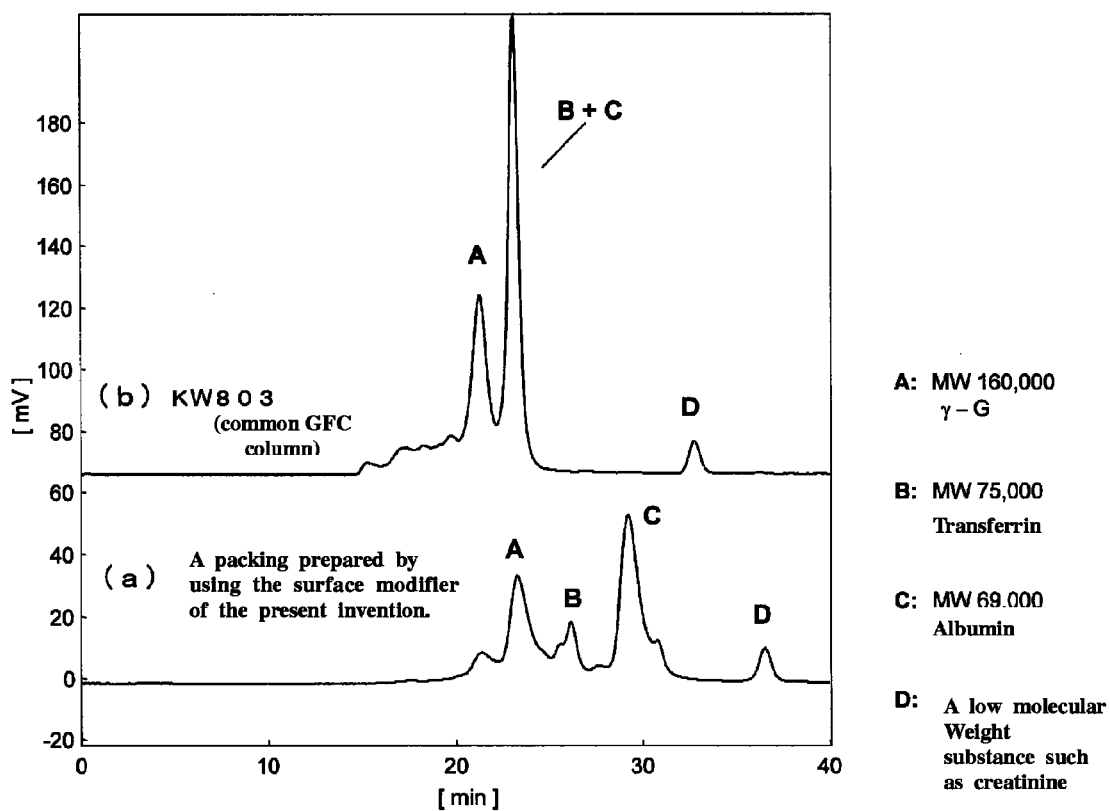
FIG. 8 is a chromatogram showing separation of human serum proteins wherein the mobile phase salt concentration is 150 mM. (a) A packing synthesized by using the surface modifier of the present invention. (b) Shodex PROTEIN KW803.

Furthermore, FIG. 8(a) shows a chromatogram when a packing prepared by the surface modifier of the present invention is used with a salt concentration of 150 mM, and FIG. 8(b) shows a chromatogram when Shodex PROTEIN KW803 is used with a salt concentration of 150 mM. Conditions for FIG. 8 other than the salt concentration are the same as those for FIG. 7.

A substantial characteristic of the chromatogram that uses the packing prepared by using the surface modifier of the present invention (FIG. 7(a)) is that the transferrin peak is verified as a shoulder in addition to γ-globulin and albumin, which are major proteins in human serum. The peak assignment was carried out by using a commercially available sample of each protein.

In contrast, when a conventional packing for GFC is used (FIG. 7(b)), albumin and transferrin are not separated at all. This was confirmed by the fact that commercially obtained samples of these proteins separately show the same elution time.

The molecular weights of albumin and transferrin are approximately 69,000 and 75,000 respectively, indicating that they have similar molecular weights. Conventional GFC columns cannot separate samples with similar molecular weights, such as albumin and transferrin. The packing prepared by using the surface modifier of the present invention is shown not only to have very little protein adsorption but also to be able to separate proteins having similar molecular weights based on the difference in the isoelectric point and hydrophobicity because it has subtle ionic interactions with proteins due to the dual electrical charge of the phosphorylcholine group.

That is, the chromatography packing of the present invention is shown to be able to separate samples in the GFC mode based not only on differences in the molecular weight but also on differences in the isoelectric point and hydrophobicity.

The fact that the packing prepared by using the surface modifier of the present invention has subtle ion-exchange interactions can be verified by lowering the salt concentration of the mobile phase.

In FIG. 7(a), for which the salt concentration of the mobile phase is 500 mM, transferrin is only recognized as a shoulder of the albumin peak; however, in FIG. 8(a), for which the salt concentration of the mobile phase is lowered to 150 mM, baseline separation of transferrin and albumin peaks is achieved.

Furthermore, peaks from many proteins can be observed in FIG. 8(a). Generally, the ion-exchange interactions between materials in the mobile phase and the packing surface are known to intensify as the salt concentration in the mobile phase decreases. This means that the lower the salt concentration, the stronger the material subject to the ion-exchange interactions is retained. The packing prepared by using the surface modifier of the present invention achieved complete separation of albumin and transferrin by lowering the salt concentration in the mobile phase to create strong retention of albumin.

The fact that the packing prepared by using the surface modifier of the present invention retained albumin, which is negatively charged at neutral pH in FIG. 7 and FIG. 8, under a low salt concentration seems to indicate that this packing has the anion-exchange mode.

Figure 9:
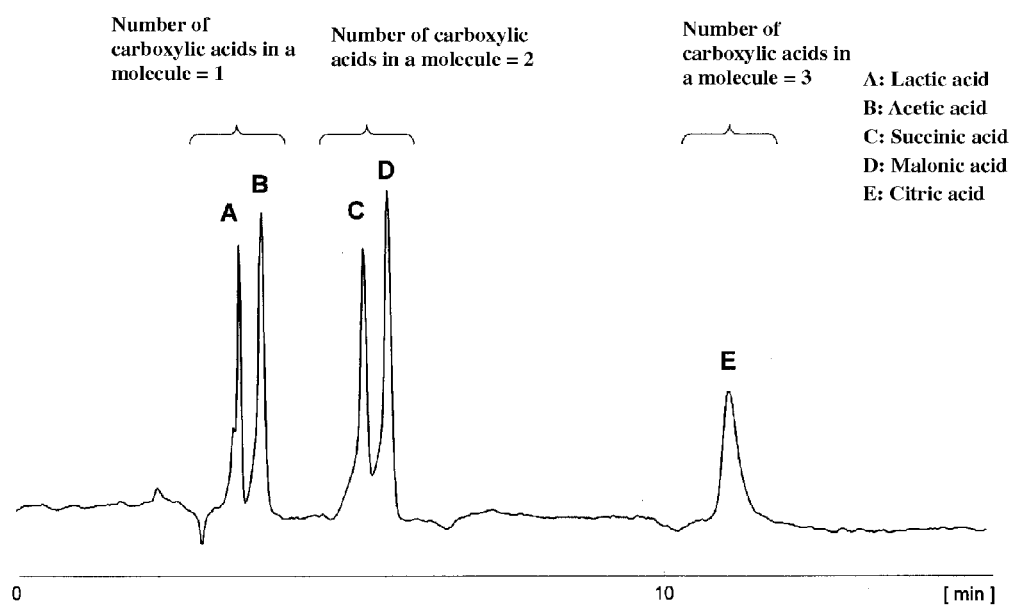
FIG. 9 is a chromatogram showing separation of five kinds of organic acid by using a packing synthesized by using the surface modifier of the present invention.

Next, the anion-exchange ability of the packing prepared by using the surface modifier of the present invention was evaluated by using five organic acids, i.e. lactic acid, acetic acid, succinic acid, malonic acid, and citric acid. The evaluation conditions are as follows: The result is shown in FIG. 9.

Column: 4.6×150 mm

Mobile phase: 50 mmol/L phosphate buffer (pH 6.8)

Flow rate: 1,000 mL/min

Detection: UV 210 nm

FIG. 9 indicates that the packing prepared using the surface modifier of the present invention can separate various organic acids based on the number of carboxylic acids.

Specifically, peaks assigned to the five kinds of carboxylic acid indicate that two kinds of organic acid having one carboxylic acid elute fastest, followed by two kinds of organic acid having two carboxylic acids, and finally citric acid, which has three carboxylic acids. Since the retention is observed to have a tendency to increase as the number of carboxylic acids increases, it is clear that this packing has the anion exchange ability. Therefore, it can be said that the powder treated with the surface modifier of the present invention is very effective as packing for anion exchange. The ion exchange ability shown above is not strong enough to adsorb and/or denature proteins, which makes it suitable for unique separation with a high recovery yield.

In contrast, a common GFC column Shodex PROTEIN KW803, as shown in FIG. 8(b), cannot separate transferrin and albumin even at a salt concentration of 150 mM.

The packing prepared by using the surface modifier of the present invention is a very unique packing that has the ion exchange mode in addition to the GFC mode (size exclusion mode) using a superior function of suppressing protein adsorption. Since there is very little protein adsorption, protein separation and purification can be done with enzyme activity intact and no denaturation of proteins. Furthermore, since there is not only the GFC mode but also the ion exchange mode, this packing is a very unique innovative packing that allows separation control based on the salt concentration and pH of the mobile phase.

Example 4

Chromatography Packing (Surface modification of a chemical compound having two nitrogen atoms between the silicon atom and the phosphorylcholine group: R in formula (1) is formula (4) (p=1).)

7.5 g of the compound of Synthesis example 1 was dissolved in 30 mL of dehydrated methanol, and the air inside the vessel is replaced by dry nitrogen. Next, 3.6 g of 3-(2-aminoethylaminopropyl)trimethoxysilane (from Shin-Etsu Chemical Co., Ltd.) was added to a methanol solution of compound 1.

This mixed solution was stirred for five hours at room temperature and cooled with ice; 2.5 g of sodium cyanohydroborate is then added and the temperature is returned back to room temperature, followed by 16 hours of stirring. During this time dry nitrogen was continued to be fed through the reaction vessel.

After filtering the precipitation, a methanol solution of the target materials, i.e. the compound of the following formulas (12) and (13), was obtained.

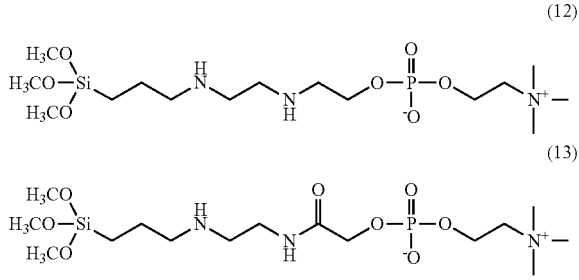

35 mL of distilled water was added to a methanol solution containing the compounds of formulas (12) and (13), to which 14 g of silica gel having an average particle size of 5 micrometers, average fine pore size of 30 nm, and specific surface area of 140 m$^2$/g was added. This powder dispersion solution is refluxed for five hours at 80° C. After the refluxing, filtering and rinsing are carried out using 100 mL of methanol to obtain the target material.

Figure 10:
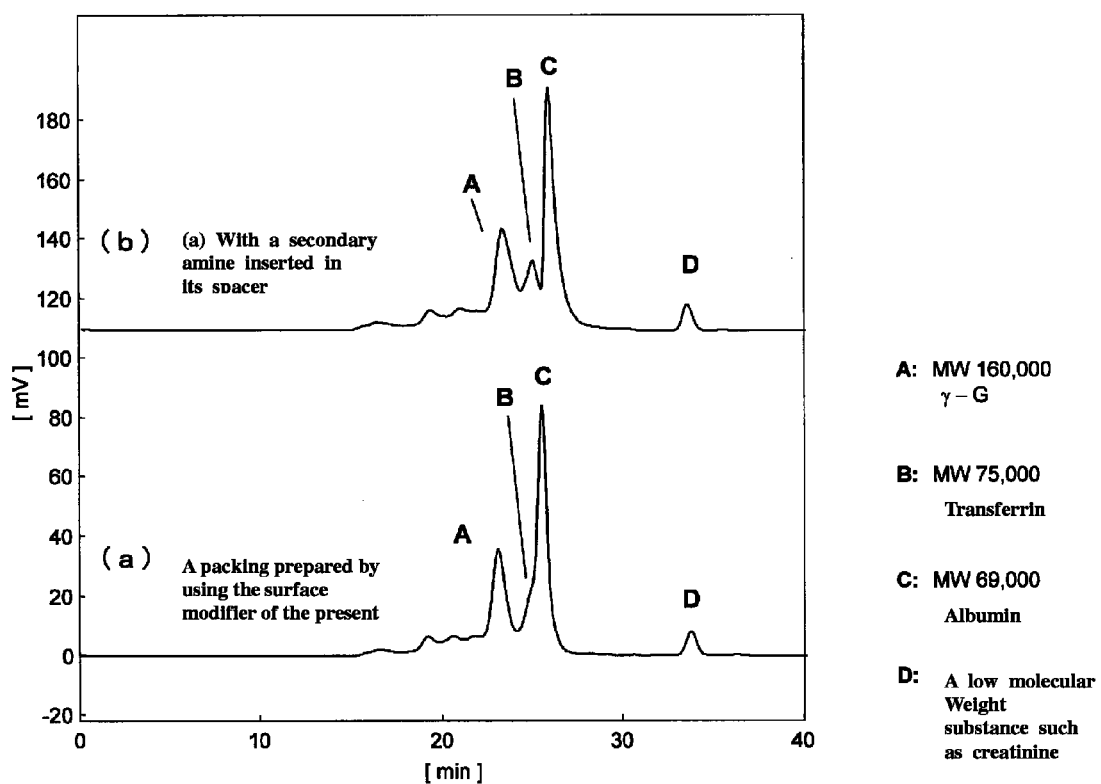
FIG. 10 is a chromatogram showing separation of human serum proteins wherein a secondary amine is inserted in the spacer portion of the surface modifier of the present invention.

FIG. 10(b) shows a chromatogram for a human serum sample (Consera N, product name, diluted two times with physiological distilled water) injected into a column filled by means of a conventional slurry method with silica gel onto which formulas (12) and (13) were introduced.

FIG. 10(a) is a chromatogram obtained by using the powder prepared in Example 3.

The difference between Example 3 and this example lie in the fact that the number of secondary amines in the spacer portion of the surface modifier is different. Identical silica gels are used for FIGS. 10(a) and (b).

FIG. 10(b), which has one more secondary amines between the silicon atom and the phosphorylcholine group compared with FIG. 10(a), is shown to have even better separation between transferrin and albumin. This is believed to be due to the fact that the insertion of a secondary amine between the silicon atom and the phosphorylcholine group increases the basicity of the modifying group, which leads to stronger retention of albumin, which is an acidic protein.

As described above, the surface modifier of the present invention not only has the protein adsorption suppression effect due to the phosphorylcholine group but also is capable of acquiring interactions such as ion exchange, hydrophobicity, hydrophilicity, hydrogen bonding, etc. by changing the nature of the spacer between the silicon atom and the phosphorylcholine group.

Example 5

A Borosilicate Fiberglass Filter Material

<Preparation of a Borosilicate Fiberglass Filter Material Bonded with Phosphorylcholine Groups>

20 g of distilled water and 1.0 mL of a methanol solution the compound of formulas (10) and (11) prepared in Example 1 (approximately 0.4 mmol) were put into a 100 mL conical flask, followed by shaking/mixing. 8 sheets of borosilicate fiberglass filter (fiberglass filter grade GF/F, 25 mm diameter, approximately 0.070 g/sheet) from Whatman Japan Co. Ltd. were added to this, followed by heating up to 100° C. and 5 hours of reflux boiling. After cooling the temperature down to room temperature, the filters were strained, rinsed, and dried under a reduced pressure for three hours at 80° C. to obtain borosilicate fiberglass filters to which phosphorylcholine groups have been directly introduced.

<Measurement of the Protein Adsorption Suppression Effect of Filter Materials>

10 mg of bovine serum albumin (BSA) is dissolved in 100 mL of phosphate buffer (prepared by dissolving 1 tablet of PBS from Takara Bio Co. Ltd. in distilled water and adjusting the total volume to be 100 mL: pH 7.4-7.5) to obtain a BSA solution. 2.0 g of the BSA solution was put into each of 3 polypropylene 30 mL sample tubes; the borosilicate fiberglass filter prepared in Example 6 was put into one of the sample tubes and immersed, and an untreated borosilicate fiberglass filter was put into another of the sample tubes and immersed. They were left alone for 24 hours at room temperature (25° C.); the Lowry method was used to color the BSA solution sampled from each of the sample tubes and the BSA adsorption level on each filter was quantified by means of absorption spectrophotometry (Table 2).

The borosilicate fiberglass filter of the present invention was shown to have a reduced BSA adsorption level compared with the untreated filter.

TABLE 2

| Sample | BSA adsorption level (mg/sheet) |
|---|---|
| Untreated borosilicate fiberglass filter | 37.8 |
| PC-treated borosilicate fiberglass filter | 7.8 |

The results shown above indicate that the present invention provides a filter material with very little adsorption of proteins and polypeptides.

The filter material of the present invention is useful for filtration of a wide range of biological substances; examples include separation and concentration of antibodies, enzymes and the like, and blood purification and analysis such as blood dialysis and blood filtering.

Example 6

Glass Vial

<Preparation of a Glass Vial to which Phosphorylcholine Groups are Bonded>

20 g of distilled water and 1.0 mL of a methanol solution of the compound of formulas (10) and (11) prepared in Example 1 (approximately 0.4 mmol) were put into a 100 mL conical flask, followed by shaking/mixing. 10 screw-type 12×32 mm glass vials (glass vials from Nihon Waters KK) were added to this, followed by heating up to 100° C. and 5 hours of reflux boiling. After cooling the temperature down to room temperature, the vials were rinsed, and dried under a reduced pressure for three hours at 80° C. to obtain glass vials that have phosphorylcholine groups directly on the surface.

As described above, glass experimental devices having very little protein adsorption can be obtained by using the surface modifier of the present invention. When common vials, which do not suppress protein adsorption, are used, the protein sample concentration is known to decrease with time during the experiment. Specifically, when samples are injected to a liquid high performance chromatography from a storage container, a phenomenon is known in which the peak area decreases as time goes on even though the same volume is injected every time. The glass vials prepared in this example can prevent such a phenomenon since they are superior in terms of suppressing protein adsorption.

A method in which polymer is adsorbed on the inner surface of the container to suppress protein adsorption is known to have a problem in terms of durability since a sample containing an organic solvent would cause the polymer to come off. Surface coating with polymer is achieved by adsorption of the polymer onto the base material such as a polypropylene container due to the hydrophobic interaction. When the sample solvent contains an organic solvent, the hydrophobic interaction between the polymer and the base material weakens and the polymer peels off. In contrast, the surface modifier of the present invention (silane coupling agent) can achieve surface modification by means of chemical bonding and therefore the effect can be sustained without substantial influence from a solvent in the sample.

Example 7

Preparation of a Phosphorylcholine Derivative Having a Carboxyl Group 5 g (19.4 mmol) of glycerophosphorylcholine, 17 g (79.7 mmol, 4.1 eq) of sodium periodate (from Wako Pure Chemical Industries, Ltd), 81 mg (0.39 mmol, 0.02 moleq) of ruthenium trichloride (from Wako Pure Chemical Industries, Ltd), 70 g of ion-exchanged water and 30 g of acetonitrile were put into a 200 ml flask. After stirring for two hours at room temperature, filtering was carried out and the solvent was removed from the filtrate. The target substance was extracted from the obtained solid by using methanol, and then methanol was removed to obtain the phosphorylcholine derivative having a carboxyl group represented by formula (9). A $^1$H NMR spectrum of the compound of formula (9) is shown in FIG. 16 and its mass spectrum is shown in FIG. 17.

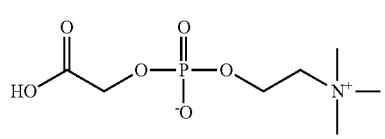

(9)

Example 8

Organic Silane Compound (Silane Coupling Agent) Having an Amide Bond Between the Silicon Atom and the Phosphorylcholine Group: R in Formula (1) is Represented by Formula (3) (L=2).

3 g (12.4 mmol) of the compound of the aforementioned formula (9) was dissolved in 100 mL of dehydrated methanol, and the air inside the vessel was replaced by dry nitrogen. Next, 1.1 g (6.2 mmol) of 3-aminopropyltrimethoxysilane, 1.4 g (12.4 mmol) of N-hydroxysuccineimide, and 2.4 g (12.4 mmol) of N-ethyl-N'-3-dimethylaminopropylcarbodiimide were added, followed by 16 hours of reaction time at −10° C., to obtain a solution containing an organic silane compound having a spacer consisting of the amide bond shown in the following formula (11) and the phosphorylcholine group at the end.

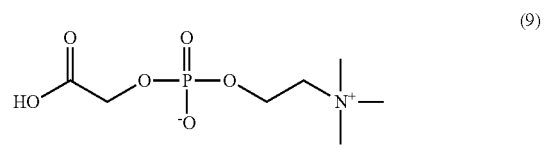

(9)

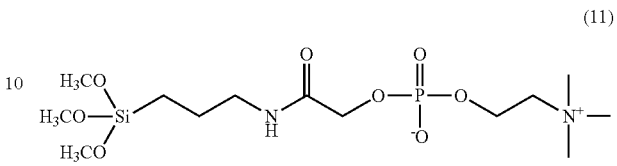

(11)

A compound represented by formula (1) wherein R is formula (3) (L=6) can be obtained by a similar procedure except for the fact that 0-phosphorylcholine hydroxyhexanoic acid, which has a saturated alkyl chain having five carbon atoms between the phosphorylcholine group and the carboxyl group, was used instead of the compound represented by the aforementioned formula (9).

The surface modifier of the present invention can be used without purification to immobilize the phosphorylcholine group on a base material. However, it can be purified using the following method, for example.

<Purification Method>

The obtained solution is concentrated under reduced pressure and dissolved in distilled water. This aqueous solution is used as a sample. A high speed liquid chromatography column Capsule Pack SCX UG80 S-5 (size: 4.6 mm i.d.×250 mm) (from Shiseido), which is capable of hydrophobic interaction and cation exchange, is connected to a HPLC apparatus and equilibrated with 0.2 mmol/L phosphate buffer at a flow rate of 1 mL/minute, followed by injection of 10 μL of the sample. A chromatogram can be obtained by using a differential refractometer as a detector, and the target chemical compound can be isolated.

Example 9

Modified Powder Treated with an Organic Silane Compound Having a Spacer Consisting of an Amide Bond and a Phosphorylcholine Group at the End 35 mL of distilled water was added to a solution (30 mL) containing the compound of formula (11) prepared in Example 8 (0.25 mmol/mL), to which 14 g of silica gel having an average particle size of 5 micrometers, average fine pore size of 30 nm, and specific surface area of 140 m$^2$/g was added. This powder dispersion solution was refluxed for five hours at 80° C. After the refluxing, filtering and rising were carried out using 100 mL of methanol to obtain the target material. The obtained modified powder treated with the surface modifier of Example 8 had a carbon content of 2.49% (the carbon content before treatment was 0.15%).

"Verification of the Introduction of the PC Group by Means of Quantification of Phosphorus"

Quantification of the phosphorus element was carried out for the modified powder having phosphorylcholine groups on the surface prepared in Example 9. In the preparation method of the present invention, the phosphorus element exists only in the phosphorylcholine group and therefore the introduction of the phosphorylcholine group can be verified by quantifying the phosphorus element present on the powder surface. Quantification of the phosphorus element was carried out by means of the molybdic acid color development method. The quantification method is described below.

(1) A prescribed amount of the powder is measured out and put into a thoroughly rinsed test tube.
(2) 3 mL of 60% aqueous solution of perchloric acid (from Wako Pure Chemical Industries, Ltd) is added to the powder of (1).
(3) In order to prevent evaporation loss of the liquid, a cooling tube is attached to the upper part of the test tube of (2), and the sample is heated for one hour at 120° C. and then for two hours at 180° C. This manipulation oxidizes all the modifying chains on the powder surface and the phosphorus is freed as phosphoric acid.
(4) The solution of (3) is centrifuged (3,000 rpm, five minutes) and 1 mL of the supernatant is transferred to a sample tube.
(5) 1 mL of distilled water, 500 g L of 0.5 M sodium molybdate (from Wako Pure Chemical Industries, Ltd), and 500 μL of 0.5 M ascorbic acid are added to the solution of (4).
(6) The solution of (5) is heated in a 95° C. hot water bath for five minutes, followed by cooling with cold water.
(7) 200 μL of the color-developed solution of (6) is dripped onto a 96-well plate and the color intensity at 710 nm is measured with a plate reader.
(8) The amount of phosphorus element in the sample is quantified based on a calibration curve obtained from the color intensity of a phosphoric acid solution having a known concentration. A standard solution of phosphoric acid can be obtained from Wako Pure Chemical Industries, Ltd As a result, the amount of the phosphorus element in the modified powder having phosphorylcholine groups on the surface prepared in Example 9 was 0.13 mmol/$g_{gel}$. This means 0.13 mmol/$g_{gel}$ of phosphorylcholine groups were successfully immobilized on the powder surface.

Figure 11:
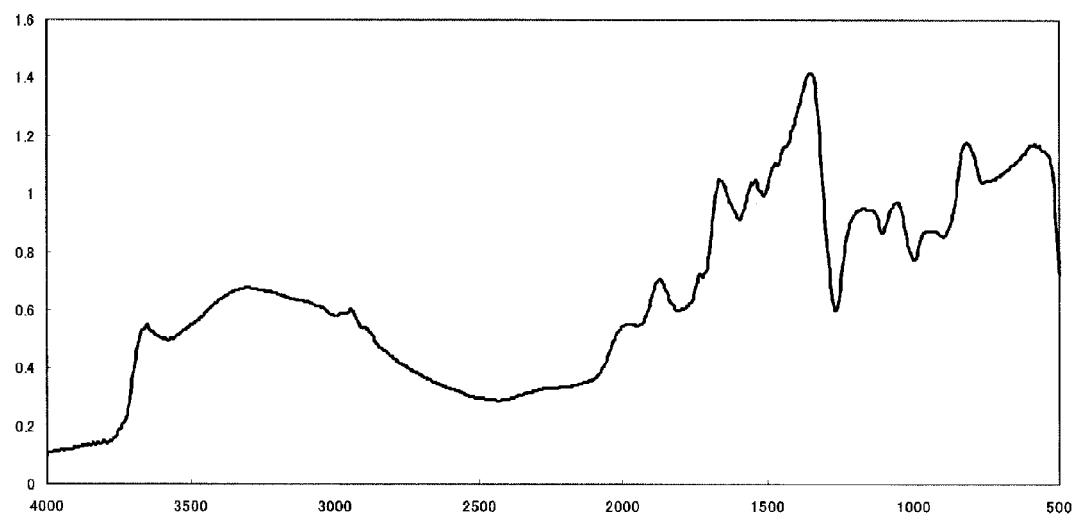
FIG. 11 is a FT-IR spectrum of the modified powder prepared in Example 9.

FIG. 11 shows a FT-IR spectrum of the modified powder synthesized in this Example.

Absorption specific to amide bonding is observed near 1650 cm$^{-1}$.

Example 10

A Liquid Chromatography Packing Treated with a Surface Modifier (Silane Coupling Agent) Having a Spacer Consisting of an Amide Bond and a Phosphorylcholine Group at the End The modified powder synthesized in Example 9, as a carrier, was put into an empty column having an inner diameter of 4.6 mm and a length of 250 mm by means of a common slurry method. The acquisition conditions of the chromatogram are as follows.

Figure 12:
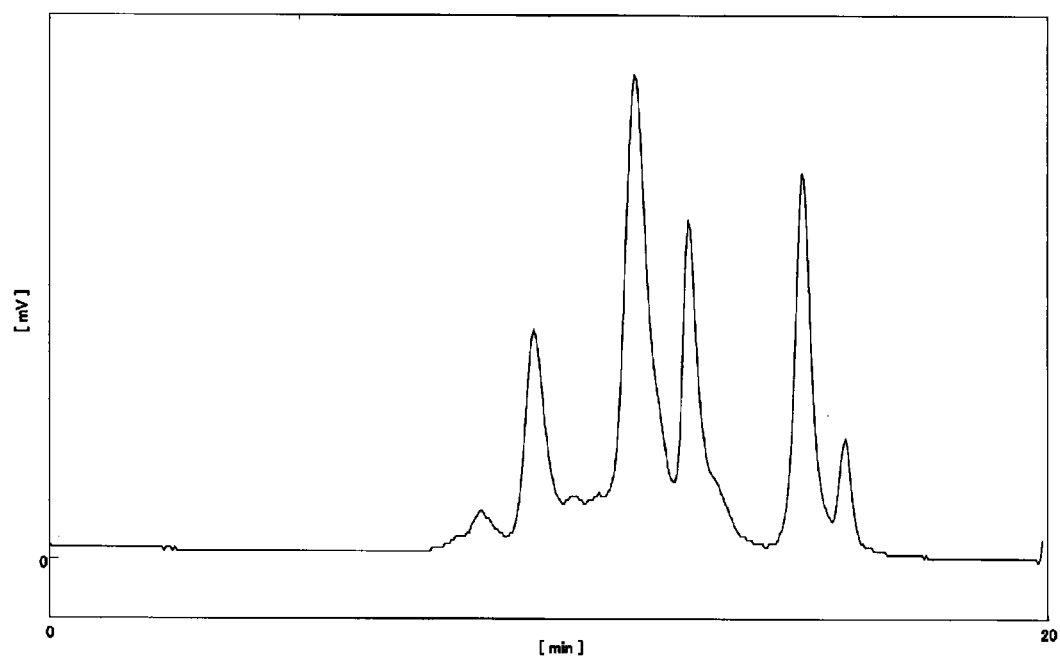
FIG. 12 is a chromatogram using the liquid chromatography packing prepared in Example 10.

Mobile phase: 50 mmol/L phosphate buffer+500 mmol/L NaCl (pH 6.9)
Flow rate: 200 μL/min
Temperature: 25° C.
Detection: UV 280 nm A chromatogram is shown in FIG. 12 for 2 μL of an injected aqueous mixed solution sample having 0.67 mg/mL α-2 macroglobulin (molecular weight approximately 800,000, abbreviated as α-2M), 1.3 mg/mL γ-globulin (molecular weight approximately 160,000, abbreviated as γ-G), 1.7 mg/mL human serum albumin (molecular weight approximately 70,000, abbreviated as HSA), 0.3 mg/mL lysozyme (molecular weight approximately 14,000, abbreviated as LYZ), and 0.017 mg/mL uracil (molecular weight 112, abbreviated as U). α-2M, γ-G, HSA, and LYZ were obtained from Sigma Aldrich Japan, and uracil was obtained from Nakalai Tesque. Five peaks were clearly observed; they were identified, using the elution times of commercial single samples, as α-2M, γ-G, HSA, LYZ, and U in ascending order of the elution time. Small peaks observed other than the five peaks are impurities contained in commercially available standard samples. Since the phosphorylcholine group is immobilized on silica gel via the amide bond, there is less protein adsorption and therefore the interaction between the packing surface and proteins is very weak, resulting in the GFC mode separation, in which molecules having a larger molecular weight elute first.

The amide bond has good hydrophilic properties. In order to suppress protein adsorption, it is desirable to cover the material surface with hydrophilic and non-ionic functional groups. A phosphorylcholine group has excellent hydrophilicity characteristics of zwitter ions and the balance charge of a zwitter ion makes its effective ionic nature very weak, making it a functional group superior in terms of protein adsorption suppression. However, if the spacer used to immobilize phosphorylcholine groups on the material surface is highly hydrophobic, then non-specific irreversible adsorption of proteins is induced. Therefore, the presence of an amide bond in the spacer is very important, achieving more hydrophilic surface modification. This hydrophilicity including the spacer's contribution is very effective in suppressing protein adsorption.

<Comparison with a Surface Modifier Having the Betaine Structure (Comparison with Prior Art)>

Comparative Example 2

For an organic silane surface modifier having the betaine structure, which is different from a phosphorylcholine group, Japanese Patent Laid-Open No. H05-222064 bulletin discloses a silane compound having sulfobetaine represented by formula (14). Also, Japanese Patent Laid-Open No. S63-295593 bulletin discloses a silane compound having carboxybetaine represented by formula (15).

The silane compounds of formulas (14) and (15) were compared with compounds of formulas (10) and (11) of Example 1.

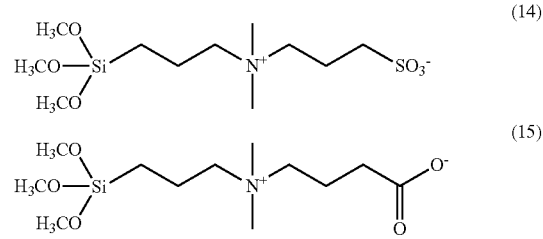

Compounds of formulas (14) and (15) were prepared by following a method described in corresponding publicly known literature.

20 mL of methanol and 20 mL of distilled water were added to the compound of formula (14), to which 5.0 g of silica gel having an average particle size of 5 micrometers, average fine pore size of 30 nm, and specific surface area of 140 m$^2$/g was added. This powder dispersion solution was refluxed for five hours at 80° C. and the compound represented by formula (14) was immobilized on silica gel. After the refluxing, 50 mL of methanol was used for filtering and rinsing to obtain silica gel whose surface was modified by the compound represented by formula (14).

The same procedure was applied to the compound represented by formula (15) to obtain silica gel whose surface was modified by the compound represented by formula (15).

The obtained surface-modified silica gel was put into an empty column having an inner diameter of 4.6 mm and a length of 250 mm by means of a common slurry method. The acquisition conditions of the chromatogram are as follows.

Figure 13:
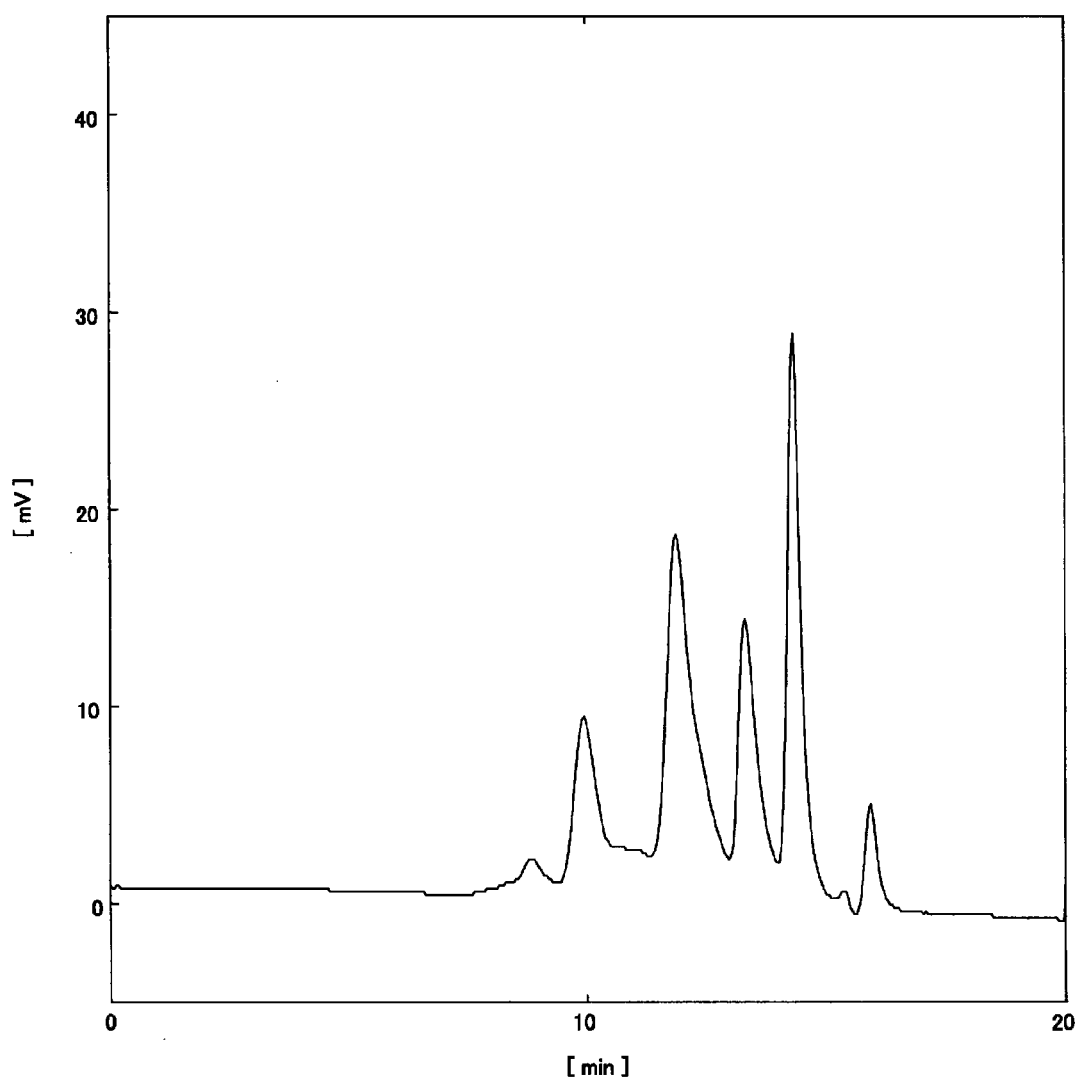
FIG. 13 is a chromatogram using the liquid chromatography packing prepared in Example 3.

Mobile phase: 50 mmol/L phosphate buffer+500 mmol/L NaCl (pH 6.9)
Flow rate: 200 μL/min
Temperature: 25° C.
Detection: UV 280 nm A column filled with the packing of Example 3 having phosphorylcholine groups on the surface was used to obtain a chromatogram shown in FIG. 13 for 2 μL of an injected aqueous mixed solution sample having 0.67 mg/mL α-2 macroglobulin (molecular weight approximately 800,000, abbreviated as α-2M), 1.3 mg/mL γ-globulin (molecular weight approximately 160,000, abbreviated as γ-G), 1.7 mg/mL human serum albumin (molecular weight approximately 70,000, abbreviated as HSA), 0.3 mg/mL lysozyme (molecular weight approximately 14,000, abbreviated as LYZ), and 0.017 mg/mL uracil (molecular weight 112, abbreviated as U). α-2M, γ-G, HSA, and LYZ were obtained from Sigma Aldrich Japan, and uracil was obtained from Nakalai Tesque.

Five peaks were clearly observed; they were identified, using the elution times of single samples, as α-2M, γ-G, HSA, LYZ, and U in ascending order of the elution time. As described thus far, this is the GFC mode in which substances having larger molecular weights elute first. Small peaks observed other than the five peaks are impurities contained in commercially available standard samples.

Figure 14:
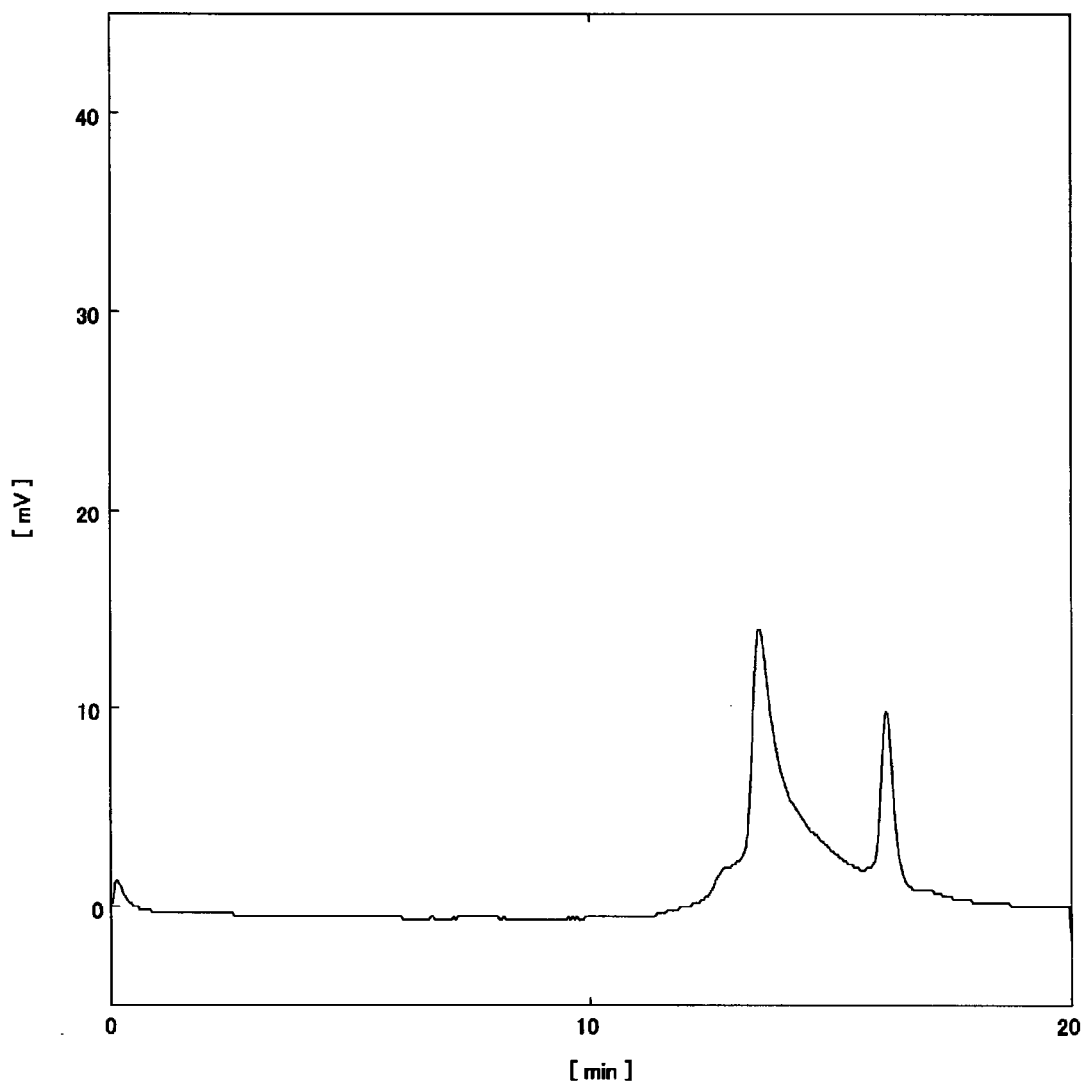
FIG. 14 is a chromatogram using the liquid chromatography packing whose surface is modified with the compound represented by formula (14) prepared in Comparative example 2.

In contrast, FIG. 14 shows a chromatogram for the same injected sample when the column was filled with a packing on which sulfobetaine represented by formula (14) was immobilized. Out of the five substances, only human serum albumin and uracil produced observable peaks; in particular, elution of lysozyme could not be confirmed at this sample concentration. This is because electrical neutrality is not established between quaternary ammonium and sulfonic acid, which are constituents of sulfobetaine, and a strong cation exchange capacity is manifested due to sulfonic acid, a strong acid, at the end, giving rise to a very strong ion exchange interaction with lysozyme, which is positively charged at neutral pH.

Figure 15:
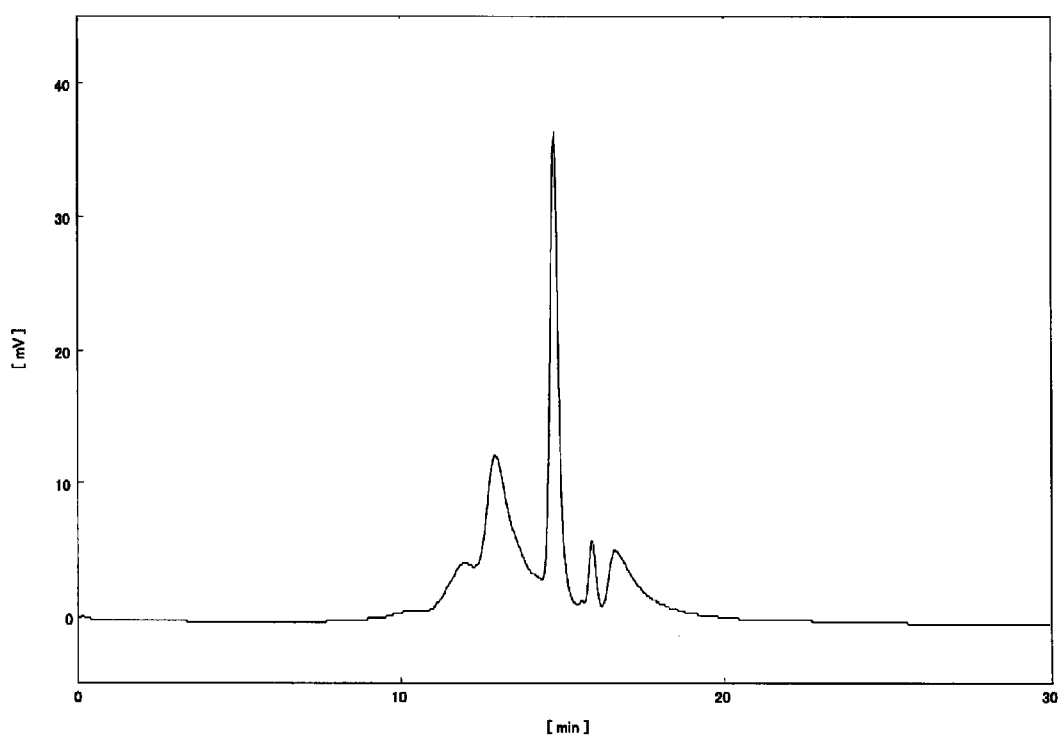
FIG. 15 is a chromatogram using the liquid chromatography packing whose surface is modified with the compound represented by formula (15) prepared in Comparative example 2.

FIG. 15 shows a chromatogram for the same injected sample when the column was filled with a packing on which carboxybetaine represented by formula (15) was immobilized. The five peaks eluted more nicely compared with when the column having sulfobetaine immobilized on it was used; they eluted in order of α-2M, γ-globulin, lysozyme, uracil, and human serum albumin. What calls for attention here is the fact that human serum albumin, which is negatively charged in the neutral pH mobile phase, was characteristically retained and eluted after uracil, which has a lower molecular weight. This is because electrical neutrality is not established between the quaternary ammonium and the carboxyl group, which are constituents of sulfobetaine, and a strong anion exchange capacity is manifested due to the more strongly ionic quaternary ammonium, giving rise to a very strong ion exchange interaction with human serum albumin, which is negatively charged at neutral pH.

As described above, the well known betaine is not perfectly neutral in the ionic sense. Some betaine structures, such as sulfobetaine and carboxybetaine, which are described here as examples, have superior hydrophilicity, but at the same time induce protein adsorption due to too much ion exchange capacity. On the other hand, the phosphorylcholine group has a suitable charge balance between the phosphoric acid and the quaternary ammonium and is shown to have a superior ability to suppress protein adsorption due to superior hydrophilicity specific to the betaine structure and also the non-ionic nature.

As described thus far, it can be said that an organic silane-type surface modifier (silane coupling agent) is very effective for material surface modification for the purpose of preventing protein adsorption. By using the surface modifier of the present invention, surface modification with less protein adsorption and superior biocompatibility can be carried out.

INDUSTRIAL APPLICABILITY

The new chemical compound of the present invention containing phosphorylcholine groups is useful as a surface modifier. The surface modifier of the present invention gives biocompatibility, moisture retaining properties, and other various useful functions to objects. The surface modifier of the present invention can be used to easily manufacture modified powder modified with phosphorylcholine groups, a chromatography packing utilizing said modified powder as a carrier, a filter modified with said surface modifier, and glass devices modified with said surface modifier.

The invention claimed is:

1. A phosphorylcholine group-containing chemical compound represented by the following formula (1):

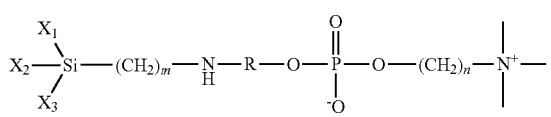

wherein, m denotes 2-6 and n denotes 1-4,
$X_1$, $X_2$, and $X_3$, independent of each other, denote a methoxy group, ethoxy group, or halogen;
up to two of $X_1$, $X_2$, and $X_3$ can be any of the following groups: a methyl group, ethyl group, propyl group, isopropyl group, butyl group, or isobutyl group;
R is a structure represented by the following formula (2) (the chemical compound of formula (1) in the structure of formula (2) being expressed as A-R—B):

$$A\text{-}(CH_2)_L\text{—}B \qquad (2)$$

wherein, in formula (2), L is 1-6.

2. A phosphorylcholine group-containing chemical compound represented by the following formula (5):

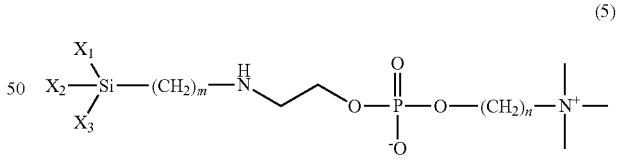

wherein, in formula 5, m denotes 2-6; n denotes 1-4; $X_1$, $X_2$, and $X_3$, independent of each other, denote a methoxy group, ethoxy group, or halogen; and up to two of $X_1$, $X_2$, and $X_3$ can be any of the following groups: a methyl group, ethyl group, propyl group, isopropyl group, butyl group, or isobutyl group.

3. A surface modifier consisting of the phosphorylcholine group-containing chemical compound of claim 1.

4. A surface modifier consisting of the phosphorylcholine group-containing chemical compound of claim 2.

* * * * *